US012736519B2

(12) United States Patent
Muller et al.

(10) Patent No.: US 12,736,519 B2
(45) Date of Patent: Sep. 15, 2026

(54) GROUP-TYPE ANALYSIS OF HYDROCARBON SAMPLES

(71) Applicant: Saudi Arabian Oil Company, Dhahran (SA)

(72) Inventors: Hendrik Muller, Al Khubar (SA); Mansour Al-Herz, Al Ahsa (SA); Nadrah A. Alawani, Al-Qatif (SA); Saroj Kumar Panda, Dhahran (SA); Lianhui Ding, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 518 days.

(21) Appl. No.: 18/469,982

(22) Filed: Sep. 19, 2023

(65) Prior Publication Data

US 2025/0093324 A1 Mar. 20, 2025

(51) Int. Cl.
*G01N 33/28* (2006.01)
*G01N 30/02* (2006.01)
*G01N 30/88* (2006.01)

(52) U.S. Cl.
CPC ........... *G01N 33/287* (2013.01); *G01N 30/02* (2013.01); *G01N 2030/025* (2013.01); *G01N 2030/8854* (2013.01)

(58) Field of Classification Search
CPC .................................................... G01N 33/287
See application file for complete search history.

(56) References Cited

U.S. PATENT DOCUMENTS

| | | | |
|---|---|---|---|
| 7,598,487 | B2 | 10/2009 | Qian et al. |
| 8,682,597 | B2 | 3/2014 | Brown et al. |
| 2003/0180963 | A1 | 9/2003 | Evans et al. |
| 2007/0050154 | A1 | 3/2007 | Tareq |
| 2008/0173804 | A1 | 7/2008 | Indo et al. |
| 2009/0059995 | A1 | 3/2009 | Burian et al. |
| 2010/0204925 | A1 | 8/2010 | Albahri |
| 2015/0107331 | A1 | 4/2015 | Wang et al. |
| 2022/0412903 | A1 | 12/2022 | Muller et al. |
| 2023/0176018 | A1 | 6/2023 | Muller et al. |

OTHER PUBLICATIONS

Adam et al., "Towards Comprehensive Hydrocarbons Analysis of Middle Distillates by LC-GCxGC," Journal of Chromatographic Science, Nov./Dec. 2007, 45:643-649, 7 pages.

International Search Report and Written Opinion in International Appln. No. PCT/US2024/047239, mailed on Nov. 27, 2024, 13 pages.

Adam et al., "Supercritical fluid chromatography hyphenated with twin comprehensive two-dimensional gas chromatography for ultimate analysis of middle distillates," Journal of Chromatography A, 2010, 1217:1386-139, 9 pages.

Akhlaq et al., "Detailed analysis of crude oil group types using reversed-phase high-performance liquid chromatography," Journal of Chromatography A, Aug. 19, 1994, 677(2):265-272, 8 pages.

Akhlaq, "Rapid group-type analysis of crude oils using high-performance liquid chromatography and gas chromatography," Journal of Chromatography A, Aug. 6, 1993, 644(2):253-258, 6 pages.

Alawani et al., "Characterization of Crude Oils through Alkyl Chain-Based Separation by Gel Permeation Chromatography and Mass Spectrometry," Energy & Fuels, 2020, 34(5):5414-5425, 12 pages.

Alawani et al., "Evaluation of Polycyclic Aromatic Hydrocarbon Removal from Hydrocracking Recycle Streams," Energy & Fuels, Dec. 24, 2019, 34(1):179-187, 9 pages.

Ali et al., "Application of high performance liquid chromatography for hydrocarbon group type analysis of crude oils," Fuel Science & Technology International, 1994, 12(1):21-33, 13 pages.

Ali et al., "Hydrocarbon Group Types Analysis of Petroleum Products: A Comparative Evaluation of HPLC and TLC Analytical Performance," Petroleum Science and Technology, Jan. 2002, 20(7-8):771-782, 12 pages.

Beckey et al., "Field desorption mass spectrometry: A technique for the study of thermally unstable substances of low volatility," Ion Phys. Journal of Mass Spectrometry and Ion Physics, 1969, 2:500-503, 3 pages.

Behrenbruch et al., "Classification and characterisation of crude oils based on distillation properties," Journal of Petroleum Science and Engineering, 2007, 57(1-2):166-180, 15 pages.

Boduszynski, "Composition of Heavy Petroleums. 1. Molecular Weight, Hydrogen Deficiency, and Heteroatom Concentration as a Function of Atmospheric Equivalent Boiling Point up to 1400° F. (760° C.)," Energy Fuels, Jan. 1, 1987, 1:2-11, 10 pages.

cdn.standards.iteh.ai [online], "Standard Test Method for Boiling Point Distribution of Samples with Residues Such as Crude Oils and Atmospheric and Vacuum Residues by High Temperature Gas Chromatography," ASTM-D7169-20, Published on Jun. 2020, originally approved in 2005, retrieved on May 9, 2024, retrieved from URL <https://cdn.standards.iteh.ai/samples/106937/3c9e8ebc45b24532b374dle516f387af/ASTM-D7169-20el.pdf>, 11 pages. cdn.standards.iteh.ai [online], "Standard Test Method for Density, Relative Density, and API Gravity of Liquids by Digital Density Meter," ASTM-D4052-22, Published on May 2022, originally approved in 1981, retrieved on May 9, 2024, retrieved from URL <https://cdn.standards.iteh.ai/samples/112378/1e427858c52b4fff89a470b85eeda29d/ASTM-D4052-22.pdf>, 5 pages.

cdn.standards.iteh.ai [online], "Standard Test Method for Detailed Analysis of Petroleum Naphthas through n-Nonane by Capillary Gas Chromatography," ASTM-D5134-21, Published on Dec. 2021, originally approved in 1990, retrieved on May 9, 2024, retrieved from URL <https://cdn.standards.iteh.ai/samples/111381/db3a51clf7b6453b99e66aac6cld5cb3/ASTM-D5134-21.pdf>, 7 pages.

(Continued)

*Primary Examiner* — Golam M Shameem
(74) *Attorney, Agent, or Firm* — Fish & Richardson P.C.

(57) ABSTRACT

The present disclosure relates to methods for reactivity-based group-type analysis of a hydrocarbon sample. An exemplary method includes determining a representative composition of each of two or more portions of the sample, determining a mass fraction of each of the two or more portions present in the sample, and determining a mass fraction of each representative species present in each of the two or more portions of the sample.

28 Claims, 12 Drawing Sheets

(56) References Cited

OTHER PUBLICATIONS cdn.standards.iteh.ai [online], "Standard Test Method for Determination of Aromatic Hydrocarbon Types in Middle Distillates-High Performance Liquid Chromatography Method with Refractive Index Detection," ASTM-D6591-19, Published Aug. 2019, originally approved in 2000, retrieved on May 9, 2024, retrieved from URL <https://cdn.standards.iteh.ai/samples/103777/54458438be6a43089ca65190ec9df59c/ASTM-D6591-19.pdf>, 6 pages.

cdn.standards.iteh.ai [online], "Standard Test Method for Paraffin, Naphthene, and Aromatic Hydrocarbon Type Analysis in Petroleum Distillates Through 200° C. by MultiDimensional Gas Chromatography," ASTM-D5443-23, Published Mar. 2023, originally approved in 1993, retrieved on May 9, 2024, retrieved from URL <https://cdn.standards.iteh.ai/samples/114689/c4f0c0c1c8fc4db5a970ba9bea30a670/ASTM-D5443-23.pdf>, 7 pages.

cdn.standards.iteh.ai [online], "Standard Test Method for Sulfur in Petroleum and Petroleum Products by Energy Dispersive X-ray Fluorescence Spectrometry," ASTM-D4294-21, Published Dec. 2021, originally approved in 1983, retrieved on May 9, 2024, retrieved from URL <https://cdn.standards.iteh.ai/samples/111413/04c650321ec24e31b8a92439645fle7b/ASTM-D4294-21.pdf>, 5 pages.

cdn.standards.iteh.ai [online], "Standard Test Methods for Hydrogen Content of Light Distillates, Middle Distillates, Gas Oils, and Residua by Low-Resolution Nuclear Magnetic Resonance Spectroscopy," ASTM-D4808-17, Published Jun. 2017, originally approved in 1988, retrieved on May 9, 2024, retrieved from URL <https://cdn.standards.iteh.ai/samples/97390/5169f72fbe6845febdd355d308943a31/ASTM-D4808-17.pdf>, 2 pages.

Coutinho et al., "Rapid hydrocarbon group-type semi-quantification in crude oils by comprehensive two-dimensional gas chromatography," Fuel, May 15, 2018, 220:379-388, 10 pages.

Djokic et al., "Combined characterization using HT-GC×GC-FID and FT-ICR MS: A pyrolysis fuel oil case study," Fuel Processing Technology, Dec. 15, 2018, 182:15-25, 11 pages.

Fafet et al., "New Developments in Mass Spectrometry for Group-Type Analysis of Petroleum Cuts—First Part: Improving Quantification of Sulphured Aromatic Compounds in Middle Distillates," Oil & Gas Science and Technology—Rev. IFP, Jul.-Aug. 1999, 54(4):439-452, 14 pages.

Fafet et al., "New Developments in Mass Spectrometry for Group-Type Analysis of Petroleum Cuts—Second Part: Development and Validation of a New Inlet System for Heavy Cuts," Oil & Gas Science and Technology—Rev. IFP, Jul.-Aug. 1999, 54(4):453-462, 10 pages.

Felix et al., "Hydrocarbon Groups Type Analysis of Petroleum Products by HPLC on Specific Stationary Phases," Journal of Liquid Chromatography, Aug. 1987, 10(10):2115-2132, 18 pages.

França et al., "Speciation and quantification of high molecular weight paraffins in Brazilian whole crude oils using high-temperature comprehensive two-dimensional gas chromatography," Fuel, 2018, 234:1154-1164, 11 pages.

Gallegos et al., "Petroleum group-type analysis by high resolution mass spectrometry," Analytical Chemistry, Dec. 1, 1967, 39(14):1833-1838, 6 pages.

Gross et al., "Field desorption mass spectrometry of large multiply branched saturated Hydrocarbons," Journal of Mass Spectrometry 2001, 36:522-528, 7 pages.

Hannisdal et al., "Group-Type Analysis of Heavy Crude Oils Using Vibrational Spectroscopy in Combination with Multivariate Analysis," Ind. Eng. Chem. Res., Mar. 2, 2005, 44(5):1349-1357, 9 pages.

Hejazi et al., "Determination of the Composition of Fatty Acid Mixtures Using GC×FI-MS: A Comprehensive Two-Dimensional Separation Approach," Analytical Chemistry, Jan. 15, 2009, 81(4):1450-1458, 9 pages.

Hodgkins et al., "Hydrodearylation of Heavy Alkyl-Bridged Noncondensed Alkyl Aromatics to Recover High-Value Mono-Aromatics," Industrial & Engineering Chemistry Research, 2019, 58:19042-19049, 8 pages.

Kinney, "A system correlating molecular structure of organic compounds with their boiling points. I. Aliphatic Boiling Point Numbers," J. Am. Chem. Soc., 1938, 60:3032-3039, 8 pages.

Kinney, "A system correlating molecular structure of organic compounds with their boiling points," J. Org. Chem., 1941, 6:220-228, 9 pages.

Kinney, "Calculation of Boiling Points of Aliphatic Hydrocarbons," Ind. Eng. Chem. 1940, 32(4):559-562, 4 pages.

Kudchadker et al., "Vapor Pressure and Boiling Points of Normal Alkanes, $C_{21}$ to $C_{100}$," Journal of Chemical and Engineering Data, 1966, 11(2):253-255, 3 pages.

Kumar et al., "Mechanistic Kinetic Modeling of the Hydrocracking of Complex Feedstocks, such as Vacuum Gas Oils," Industrial & Engineering Chemistry Research, 2007, 46(18):5881-5897, 17 pages.

Li et al., "Quantitative Molecular Composition of Heavy Petroleum Fractions: A Case Study of FCC Decant Oil," Energy & Fuels, 2020, 26 pages.

Lissitsyna et al., "PIONA analysis of kerosene by comprehensive two-dimensional gas chromatography coupled to time of flight mass spectrometry," Fuel, Jan. 15, 2014, 116:716-722, 7 pages.

Mahé et al., "Overcoming the high-temperature two-dimensional gas chromatography limits to elute heavy compounds," Journal of Chromatography A, 2012, 1229:298-301, 4 pages.

Marshall et al., "Petroleomics: Chemistry of the underworld," Proceedings of the National Academy of Sciences, Nov. 25, 2008, 105(47):18090-18095, 6 pages.

Matt et al., "Planar chromatography for the hydrocarbon group type analysis of petroleum middle distillates and coal-derived products," Fuel Processing Technology, Jun. 20, 2002, 77-78:245-253, 9 pages.

Mennito et al., "Characterization of Heavy Petroleum Saturates by Laser Desorption Silver Cationization and Fourier Transform Ion Cyclotron Resonance Mass Spectrometry," Energy & Fuels, Nov. 12, 2013, 27(12):7348-7353, 6 pages.

Miquel et al., "A new method for petroleum fractions and crude oil characterization," SPE Reservoir Engineering, May 1992, 7(2):265-270, 6 pages.

Mitschke et al., "Comprehensive Gas Chromatography-Time-of-Flight Mass Spectrometry Using Soft and Selective Photoionization Techniques," Analytical Chemistry, Jul. 28, 2006, 78(18):6364-6375, 12 pages.

Muller et al., "Characterization of High-Molecular-Weight Sulfur-Containing Aromatics in Vacuum Residues Using Fourier Transform Ion Cyclotron Resonance Mass Spectrometry," Analytical Chemistry, Mar. 5, 2005, 77(8):2536-2543, 8 pages.

Muller et al., "Evaluation of Quantitative Sulfur Speciation in Gas Oils by Fourier Transform Ion Cyclotron Resonance Mass Spectrometry: Validation by Comprehensive Two-Dimensional Gas Chromatography," Journal of The American Society for Mass Spectrometry, Feb. 23, 2012, 23:806-815, 10 pages.

Muller et al., "Innate Sulfur Compounds as Internal Standard for Determining Vacuum Gas Oil Compositions by APPI FT-ICR MS," Energy & Fuels, Jun. 12, 2020, 34(7):8260-8273, 14 pages.

Muller et al., "Narrow Distillation Cuts for an Improved Characterization of Crude Oil: An Insight on Heteroatoms in Heavy Fraction Molecules," International J. Oil, Gas and Coal Technology, 2021, 26(1):40-59, 20 pages.

Muller et al., "Saturated Compounds in Heavy Petroleum Fractions," Energy & Fuels, Aug. 10, 2020, 34(9):10713-10723, 11 pages.

Ng et al., "Distributions of Aromatics, Nitrogen, and Sulfur in Cracked Liquid Products from Microactivity Tests," Energy & Fuels, Jun. 27, 2000, 14(4):945-946, 2 pages.

Peterson, "Mass Spectrometer All-Glass Heated Inlet," Analytical Chemistry, Dec. 1, 1962, 34(13):1850-1851, 2 pages.

Potgieter et al., "Analysis of oxidised heavy paraffinic products by high temperature comprehensive two-dimensional gas chromatography," Journal of Chromatography A, 2017, 1509:123-131, 9 pages.

Purcell et al., "Atmospheric Pressure Photoionization Fourier Transform Ion Cyclotron Resonance Mass Spectrometry for Complex Mixture Analysis," Analytical Chemistry, Jul. 4, 2006, 78(16):5906-5912, 7 pages.

(56) References Cited

OTHER PUBLICATIONS

Qian et al., "Characterization of large nonvolatile polyaromatic molecules by a combination of in-source pyrolysis and field desorption mass spectrometry," Energy Fuels, 2001, 15(4):949-954, 6 pages.
Qian et al., "Deducing molecular compositions of petroleum products using GC-field ionization high resolution time of flight mass spectrometry," International Journal of Mass Spectrometry, Sep. 1, 2007, 265(2-3):230-236, 7 pages.
Qian et al., "Desorption and Ionization of Heavy Petroleum Molecules and Measurement of Molecular Weight Distributions," Energy Fuels, 2007, 21:1042-1047, 6 pages.
Qian et al., "Resolution and Identification of Elemental Compositions for More than 3000 Crude Acids in Heavy Petroleum by Negative-Ion Microelectrospray High-Field Fourier Transform Ion Cyclotron Resonance Mass Spectrometry," Energy & Fuels, Aug. 28, 2001, 15(6):1505-1511, 7 pages.
Qiang et al., "Hydrocarbon group-type analysis of high boiling petroleum distillates by HPLC," Journal of Petroleum Science and Engineering, Jan. 1999, 22(1-3):31-36, 6 pages.
Reiter et al., "Characterization of crude oil by real component surrogates," Energy & Fuels, 2014, 28(8):5565-5571, 7 pages.
Revellin et al., "Specific Nitrogen Boiling Point Profiles of Vacuum Gasoils," Energy & Fuels, Oct. 14, 2005, 19(6):2438-2444, 7 pages.
Rodgers et al., "Molecular Characterization of Petroporphyrins in Crude Oil by Electrospray Ionization Fourier Transform Ion Cyclotron Resonance Mass Spectrometry," Canadian Journal of Chemistry, May 2001, 79:546-551, 6 pages.
Rodgers et al., "Petroleum Analysis," Analytical Chemistry, Apr. 29, 2011, 83(12):4665-4687, 23 pages.
Roussis et al., "Hydrocarbon Compound Type Analysis by Mass Spectrometry: On the Replacement of the All-Glass Heated Inlet System with a Gas Chromatograph," Energy & Fuels, Jan. 25, 2001, 15(2):477-486, 10 pages.
Shearer et al., "Simultaneous Measurement of Hydrocarbons and Sulfur Compounds using Flame Ionization and Sulfur Chemiluminescence Detection for Sulfur Simulated Distillation," Journal of High Resolution Chromatography, Jun. 17, 1999, 22(7):386-390, 5 pages.
Stafford et al., "A mass spectrometer all-glass heated inlet," International Journal of Mass Spectrometry and Ion Physics, Apr. 1968, 1(1):87-92, 6 pages.
Striebich et al., "Hydrocarbon Group-Type Analysis of Petroleum-Derived and Synthetic Fuels Using Two-Dimensional Gas Chromatography," Energy & Fuels, Aug. 21, 2014, 28(9):5696-5706, 11 pages.
Vendeuvre et al., "Characterisation of middle-distillates by comprehensive two-dimensional gas chromatography (GC×GC): A powerful alternative for performing various standard analysis of middle-distillates," Journal of Chromatography A, 2005, 1086(1-2):21-28, 8 pages.
Wang et al., "Detailed Chemical Composition of Straight-Run Vacuum Gas Oil and its Distillates as a Function of the Atmospheric Equivalent Boiling Point," Energy Fuels, 2016, 30(2):968-974, 7 pages.
Xavier et al., "On the use of continuous distribution models for characterization of crude oils," Latin American Applied Research, 2011, 41(4):325-329, 5 pages.
Zhou et al., "Characterization of Saturated Hydrocarbons in Vacuum Petroleum Residua: Redox Derivatization Followed by Negative-Ion Electrospray Ionization Fourier Transform Ion Cyclotron Resonance Mass Spectrometry," Energy Fuels, 2014, 28(1):417-422, 6 pages.

GROUP-TYPE ANALYSIS OF HYDROCARBON SAMPLES

TECHNICAL FIELD

The present disclosure relates to methods for reactivity-based group-type analysis of a hydrocarbon sample.

BACKGROUND

The development of hydrocarbon conversion technologies requires chemical information regarding feedstocks, intermediates, and products. Detailed and accurate chemical information can facilitate conversion parameter determination, process step evaluation, and technology optimization. In the case of processes that target petroleum streams with a wide boiling range, such as processes involving whole crude oil upgrading or residue conversion, a number of complementary analytical techniques are typically necessary to obtain a meaningful chemical description of the sample, because individual techniques can be limited with respect to accessible boiling range. Such combinations of conventional speciation methods yield many details that can be, in their totality, hard to interpret and difficult to link to overall reactivity. PIONA group-type analysis lumps molecular constituents into chemically meaningful compound families: paraffin, iso-paraffin, olefin, naphthene, and aromatic compounds. However, conventional PIONA group-type analysis is limited to $C_1$-$C_{12}$ hydrocarbons, which excludes heavier fractions and crude oils.

Therefore, there is a need for improved methods for analyzing hydrocarbon samples, such as samples having wide boiling ranges and samples including $C_{13+}$ hydrocarbons.

SUMMARY

Provided in the present disclosure is a method of analyzing a hydrocarbon sample. The method includes determining a representative composition of each of two or more portions of the sample, where each representative composition independently includes one or more representative species; determining a mass fraction of each of the two or more portions present in the sample; and determining a mass fraction of each representative species present in each of the two or more portions of the sample. Each representative species is defined by a number of carbon atoms, a number of alkyl-chain carbon atoms, a number of saturated rings, a number of aromatic rings, and a number of sulfur atoms.

DETAILED DESCRIPTION

Figure 1:
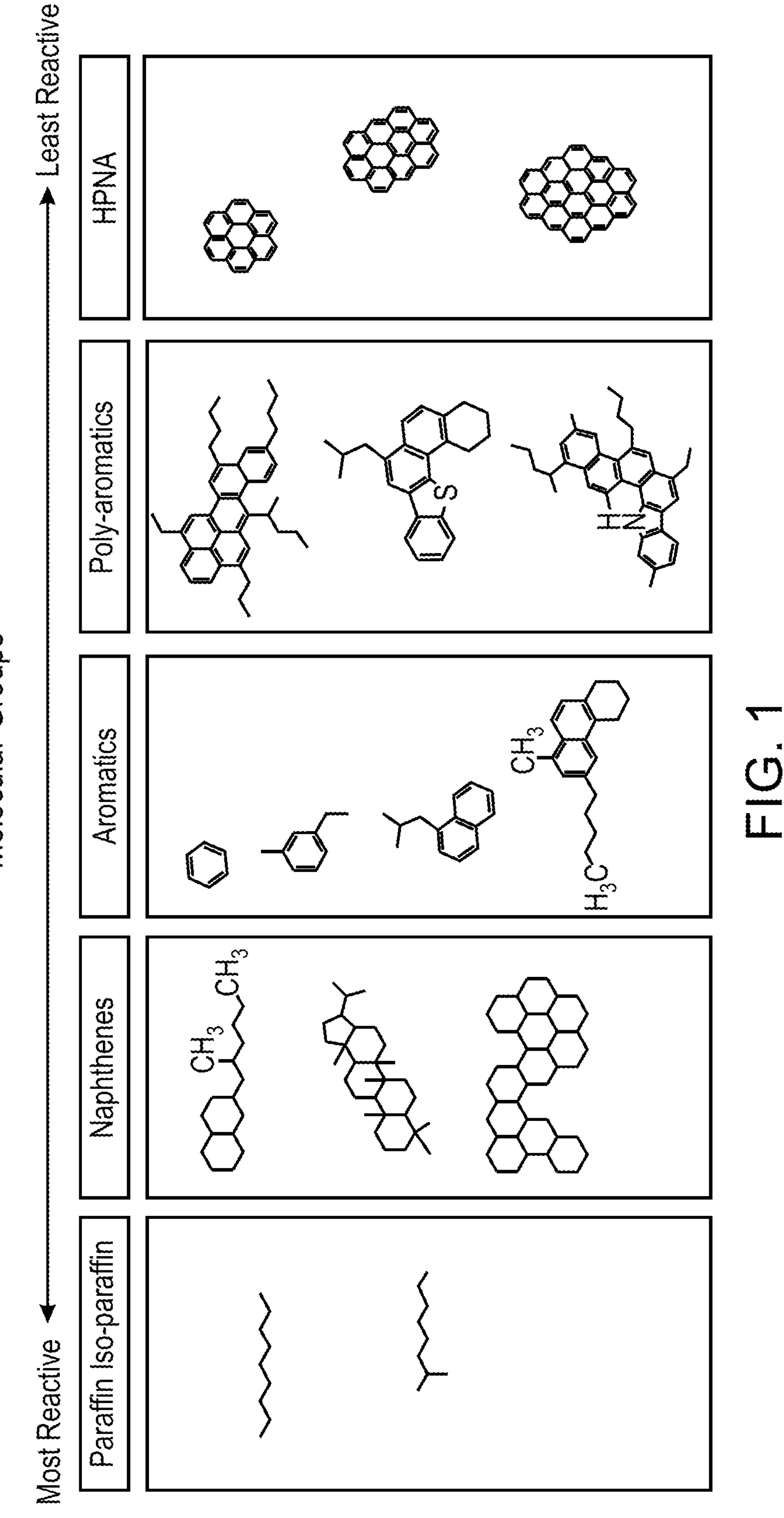
FIG. 1 shows examples of reactivity-based groups analyzed according to an embodiment of the present disclosure.

The present disclosure relates to methods for analyzing a hydrocarbon sample. The methods include determining a representative composition of each of two or more portions of the sample, each representative composition independently including one or more representative species. Each representative species is defined by a number of carbon atoms, a number of alkyl carbon atoms, a number of saturated rings, a number of aromatic rings, and a number of sulfur atoms. The method includes determining a mass fraction of each of the two or more portions present in the sample, and determining a mass fraction of each representative species present in each of the two or more portions of the sample. The methods of the present disclosure, which combine advanced speciation data with bulk properties, can provide group-type analysis of whole crude oils and petroleum-derived samples with a wide boiling profile. The analysis can provide, for example, mass fractions of reactivity-based groups including paraffins (including n- and iso-paraffins), naphthenes, aromatics, polyaromatics, and heavy polynuclear aromatics (HPNA). FIG. 1 shows examples of each group, which together can describe reactivity and coke formation for hydrocarbon samples including heavy petroleum fractions and crude oils.

Representative Species

The methods of the present disclosure include determining a representative composition of each of two or more portions of the hydrocarbon sample. Each representative composition independently includes one or more representative species, each defined by a number of carbon atoms, a number of alkyl-chain carbon atoms, a number of saturated rings, a number of aromatic rings, and a number of sulfur atoms.

In some embodiments, the one or more representative species includes a representative paraffin, representative of all n- and iso-paraffins present in a portion. For each representative paraffin, the number of carbon atoms and the number of alkyl-chain carbon atoms can be assumed to be the same. For each representative paraffin, the number of saturated rings, aromatic rings, and sulfur atoms can be assumed to be zero.

In some embodiments, the one or more representative species includes a representative naphthene, representative of all saturated compounds present in a portion that include at least one saturated ring. For each representative naphthene, the number of aromatic rings and sulfur atoms can be assumed to be zero.

In some embodiments, the one or more representative species includes a representative aromatic, representative of all compounds present in a portion that include one or two aromatic rings and do not include sulfur. For each representative aromatic, the number of sulfur atoms can be assumed to be zero.

In some embodiments, the one or more representative species includes a representative sulfur-containing aromatic, representative of all compounds present in a portion that include one or two aromatic rings, which include benzene or thiophene rings in any combination, and include at least one sulfur atom.

In some embodiments, the one or more representative species includes a representative polyaromatic, representative of all compounds present in a portion that include three aromatic rings with any number of alkyl-chain carbons, or four or more aromatic rings with four or more alkyl-chain carbons, and do not include sulfur. For each representative polyaromatic, the number of sulfur atoms can be assumed to be zero.

In some embodiments, the one or more representative species includes a representative sulfur-containing polyaromatic, representative of all compounds present in a portion that include at least one sulfur atom and three aromatic rings with any number of alkyl-chain carbons, or at least one sulfur atom and four or more aromatic rings with four or more alkyl-chain carbon atoms.

In some embodiments, the one or more representative species includes a representative heavy polynuclear aromatic (HPNA), representative of all compounds present in a portion that include four or more aromatic rings and not more than three alkyl-chain carbon atoms. For each representative HPNA, the number of saturated rings and sulfur atoms can be assumed to be zero.

Representative Composition Determination

The methods of the present disclosure include determining a representative composition of each of two or more portions of the hydrocarbon sample. In some embodiments, the method includes determining a representative composition of each of two, three, or four portions of the hydrocarbon sample. In some embodiments, the method includes determining a representative composition of each of a first portion, a second portion, a third portion, and a fourth portion of the sample.

In some embodiments, the first portion of the sample includes a light-ends fraction. In some embodiments, the first portion of the sample includes $C_1$-$C_{12}$ hydrocarbons. In some embodiments, a boiling range of the first portion of the sample is from the initial boiling point to about 230° C.

In some embodiments, the method includes determining the representative composition of the first portion of the sample by detailed hydrocarbon analysis (DHA), for example, according to ASTM-D5134, "Standard Test Method for Detailed Analysis of Petroleum Naphthas through n-Nonane by Capillary Gas Chromatography." In some embodiments, the representative composition of the first portion includes a representative paraffin, a representative naphthene, a representative aromatic, or any combination thereof. In some embodiments, the carbon number defining each representative species of the first portion is a weighted average based on the respective compounds detected by DHA. In some embodiments, the number of saturated rings defining the representative naphthene of the first portion can be assumed to be 1. In certain such embodiments, the number of aromatic rings defining the representative aromatic of the first portion can be assumed to be 1. In some embodiments, the number of alkyl-chain carbon atoms defining the representative naphthene, the representative aromatic, or both are calculated as the difference between the total carbon number and the ring-carbon content of the representative species.

In some embodiments, the second portion of the sample includes a middle-boiling fraction. In some embodiments, the second portion of the sample includes $C_6$-$C_{26}$ hydrocarbons. In some embodiments, a boiling range of the second portion of the sample is about 70° C. to about 410° C.

In some embodiments, the method includes determining the representative composition of the second portion of the sample by 2-dimensional gas chromatography (GC×GC). In some embodiments, the representative composition of the second portion includes a representative paraffin, a representative naphthene, a representative aromatic, a representative sulfur-containing aromatic, a representative polyaromatic, a representative sulfur-containing polyaromatic, a representative HPNA, or any combination thereof. In some embodiments, the carbon number defining each representative species of the second portion is a weighted average based on the respective compounds detected by GC×GC. In some embodiments, the number of saturated rings defining the representative naphthene, representative aromatic, representative sulfur-containing aromatic, representative polyaromatic, and representative sulfur-containing polyaromatic of the second portion is a weighted average based on the respective compounds detected by GC×GC. In some embodiments, the number of aromatic rings defining the representative aromatic, representative sulfur-containing aromatic, representative polyaromatic, representative sulfur-containing polyaromatic, and representative HPNA of the second portion is a weighted average based on the respective compounds detected by GC×GC. In some embodiments, the number of sulfur atoms defining the sulfur-containing aromatic and representative sulfur-containing polyaromatic of the second portion is a weighted average based on the respective compounds detected by GC×GC. In some embodiments, the number of alkyl-chain carbon atoms defining the representative naphthene, the representative aromatic, the representative sulfur-containing aromatic, the representative polyaromatic, the representative sulfur-containing polyaromatic, the representative HPNA, or any combination thereof are calculated as the difference between the total carbon number and the ring-carbon content of the representative species.

In some embodiments, the third portion includes a high-boiling fraction. In some embodiments, the third portion of the sample includes $C_{16}$-$C_{42}$ hydrocarbons. In some embodiments, a boiling range of the third portion of the sample is about 300° C. to about 550° C.

In some embodiments, the method includes determining the representative composition of the third portion of the sample by gas chromatography field ionization mass spectrometry (GC-FIMS). In some embodiments, the method includes determining the representative composition of the third portion of the sample by high-temperature GC×GC with high-resolution mass spectrometry. In some embodiments, the representative composition of the third portion includes a representative paraffin, a representative naphthene, a representative aromatic, a representative sulfur-containing aromatic, a representative polyaromatic, a representative sulfur-containing polyaromatic, a representative HPNA, or any combination thereof. In some embodiments, the carbon number defining each representative species of the third portion is a weighted average based on the respective compounds detected by GC-FIMS. In some embodiments, the number of saturated rings defining the representative naphthene, representative aromatic, representative sulfur-containing aromatic, representative polyaromatic, and representative sulfur-containing polyaromatic of the third portion is a weighted average based on the respective compounds detected by GC-FIMS. In some embodiments, the number of aromatic rings defining the representative aromatic, representative sulfur-containing aromatic, representative polyaromatic, representative sulfur-containing polyaromatic, and representative HPNA of the third portion is a weighted average based on the respective compounds detected by GC-FIMS. In some embodiments, the number of sulfur atoms defining the sulfur-containing aromatic and representative sulfur-containing polyaromatic of the third portion is a weighted average based on the respective compounds detected by GC-FIMS. In some embodiments, the number of alkyl-chain carbon atoms defining the representative naphthene, the representative aromatic, the representative sulfur-containing aromatic, the representative polyaromatic, the representative sulfur-containing polyaromatic, the representative HPNA, or any combination thereof are calculated as the difference between the total carbon number and the ring-carbon content of the representative species.

In some embodiments, the fourth portion includes a non-boiling fraction. In some embodiments, the fourth portion of the sample includes $C_{30}$-$C_{100}$ hydrocarbons. In some embodiments, a boiling range of the fourth portion of the sample is above 400° C.

In some embodiments, the method includes determining the representative composition of the fourth portion of the sample by Fourier transform ion cyclotron resonance mass spectrometry (FT-ICR MS). In some embodiments, the method includes determining the representative composition of the fourth portion of the sample by liquid chromatographic fractionation followed by field desorption/field ionization time of flight mass spectrometry (FD/FI TOFMS). In some embodiments, the representative composition of the fourth portion includes a representative paraffin, a representative naphthene, a representative aromatic, a representative sulfur-containing aromatic, a representative polyaromatic, a representative sulfur-containing polyaromatic, a representative HPNA, or any combination thereof. In some embodiments, the carbon number defining each representative species of the fourth portion is a weighted average based on the respective compounds detected by FT-ICR MS. In some embodiments, the number of saturated rings defining the representative naphthene, representative aromatic, representative sulfur-containing aromatic, representative polyaromatic, and representative sulfur-containing polyaromatic of the fourth portion is a weighted average based on the respective compounds detected by FT-ICR MS. In some embodiments, the number of aromatic rings defining the representative aromatic, representative sulfur-containing aromatic, representative polyaromatic, representative sulfur-containing polyaromatic, and representative HPNA of the fourth portion is a weighted average based on the respective compounds detected by FT-ICR MS. In some embodiments, the number of sulfur atoms defining the sulfur-containing aromatic and representative sulfur-containing polyaromatic of the fourth portion is a weighted average based on the respective compounds detected by FT-ICR MS. In some embodiments, the number of alkyl-chain carbon atoms defining the representative naphthene, the representative aromatic, the representative sulfur-containing aromatic, the representative polyaromatic, the representative sulfur-containing polyaromatic, the representative HPNA, or any combination thereof are calculated as the difference between the total carbon number and the ring-carbon content of the representative species.

Mass Fraction Determination

The methods of the present disclosure include determining a mass fraction of each of the two or more portions present in the sample, and determining a mass fraction of each representative species present in each of the two or more portion of the sample. In some embodiments, the method includes determining a mass fraction of each of a first portion, a second portion, a third portion, and a fourth portion of the sample. In certain such embodiments, the method includes determining a mass fraction of each representative species present in each of the first portion, second portion, third portion, and fourth portion of the sample.

In some embodiments, the method includes determining the mass fraction of each of the two or more portions by fitting to an actual or simulated distillation profile of the sample. The distillation profile is obtained, for example, according to ASTM D7169, "Standard Test Method for Boiling Point Distribution of Samples with Residues Such as Crude Oils and Atmospheric and Vacuum Residues by High Temperature Gas Chromatography." Fitting can be performed by calculating the average boiling point of each portion from its average molecular properties, and setting the cumulative mass fraction of this portion equal to the recovery at the corresponding distillation temperature, or using any suitable algorithm.

The bulk properties of the entire sample can arise as a combination of the molecular properties of the representative species that include each portion of the sample, whereby the contribution of each species is weighted by its concentration. For example, the total hydrogen content can be the result of the hydrogen content of all molecules in the sample, whereby the contribution of each molecule can depend on its concentration. In some embodiments, the individual representative species' concentrations, expressed as mole fractions, are not determined by the speciation methods described above, but instead are fitted as follows: initial calculations of bulk properties are performed by combining the representative species' molecular properties, assuming an equimolar concentration as initial distribution of mol fractions; mass fractions are derived from mole fractions of the individual representative species by multiplication with the respective molecular weight, and normalized to the mass fraction of the respective portion of the sample; then, the actual mole fractions and resulting mass fractions of individual representative species are iteratively adjusted to minimize an objective function representing the disparity between calculated and measured bulk properties.

In some embodiments, the method includes determining the mass fraction of each representative species present in each of the two or more portions by fitting to one bulk parameter, or to multiple bulk parameters of the sample, without adjusting the mass fractions of each of the two or more portions present in the sample as fitted in the previous step. Fitting of the representative species' mass fractions can be achieved by minimizing an objective function obtained as the summed squared differences between measured and calculated bulk properties. The bulk properties can be any combination of carbon atom type, hydrogen atom type, aromatic ring number, total sulfur content, and total hydrogen content. One or more of the bulk properties' contributions to the objective function may independently be weighted by a factor between 1 and 100, whereby a higher weight increases the importance of the respective parameter. This fitting can be performed using any suitable optimization algorithm, such as, for example, a generalized reduced gradient (GRG) algorithm or an evolutionary algorithm. In some embodiments, the fitting is performed using a GRG nonlinear algorithm.

In some embodiments, the bulk parameter includes a carbon-type distribution of the sample and a hydrogen-type distribution of the sample. The carbon-type distribution of the sample can include the relative mole fractions of each of paraffinic, naphthenic, and aromatic carbons present in the sample, and can be determined by $^{13}C$ nuclear magnetic resonance (NMR) spectroscopy. The hydrogen-type distribution of the sample can include the relative mole fractions of saturated and aromatic hydrogens present in the sample, and can be determined by $^{1}H$ NMR spectroscopy.

In some embodiments, the bulk parameter includes a saturated compound content of the sample and an aromatic compound content of the sample. The saturated compound content and aromatic compound content of the sample can include the relative mole fractions of saturated and aromatic compounds present in the sample, and can be determined by high-pressure liquid chromatography (HPLC).

In some embodiments, the bulk parameter includes a total hydrogen content of the sample, a total sulfur content of the sample, or both. The total hydrogen content of the sample can be determined according to ASTM D4808-17 "Standard Test Methods for Hydrogen Content of Light Distillates, Middle Distillates, Gas Oils, and Residua by Low-Resolution Nuclear Magnetic Resonance Spectroscopy." The total sulfur content of the sample can be determined, for example, according to ASTM D4294, "Standard Test Method for Sulfur in Petroleum and Petroleum Products by Energy Dispersive X-ray Fluorescence Spectrometry."

Hydrocarbon Samples

In some embodiments, the hydrocarbon sample has a broad boiling range, for example, from about 50° C. to about 750° C. In some embodiments, the hydrocarbon sample includes a crude oil. In some embodiments, the hydrocarbon sample includes a derivative of crude oil, such as a hydrotreated crude oil, partially hydrotreated crude oil, a crude oil distillation fraction, a partially hydrotreated distillation fraction. In some embodiments, the hydrocarbon sample includes a heavy crude oil fraction. In some embodiments, the hydrocarbon sample includes a de-asphalted crude oil, a base oil, or a slurry oil.

Figure 2:
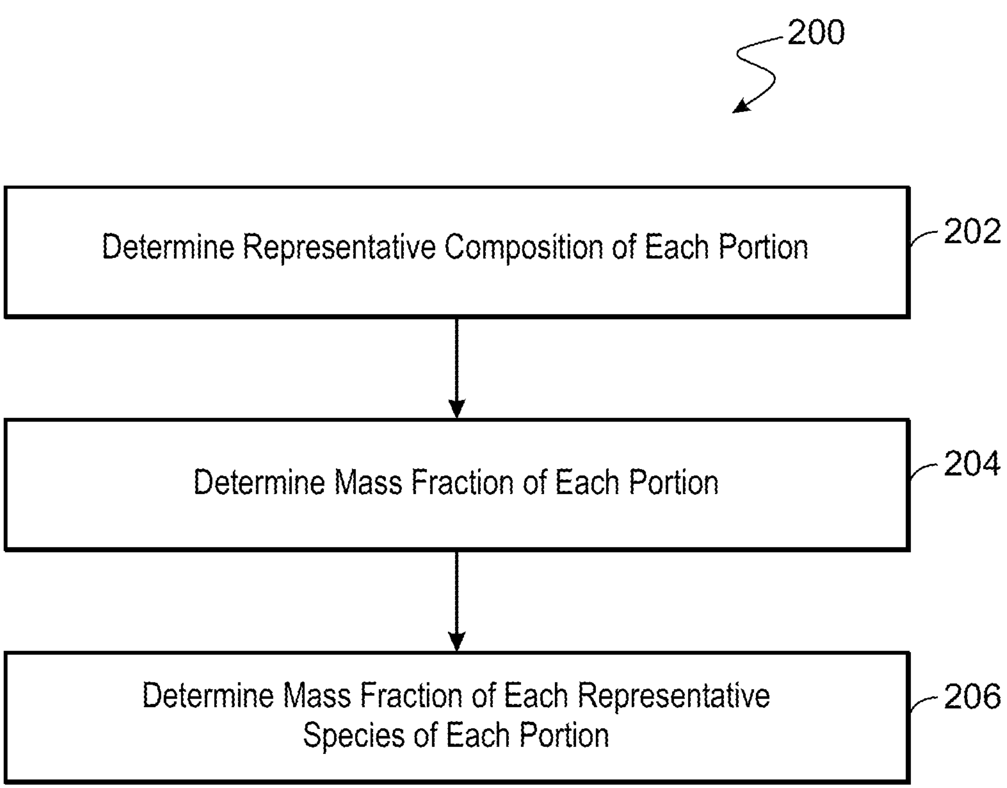
FIG. 2 is a process flow diagram of a method for analyzing a hydrocarbon sample.

FIG. 2 is a process flow diagram of a method 200 for analyzing a hydrocarbon sample. The method starts at block 202 with the determination of a representative composition of each of two or more portions of the sample, each representative composition independently including one or more representative species. At block 204 of the method, a mass fraction of each of the two or more portions present in the sample is determined. At block 206 of the method, a mass fraction of each representative species present in each of the two or more portions of the sample is determined.

Definitions

The terms "a," "an," and "the" are used in the present disclosure to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

As used in the present disclosure, the term "about" can allow for a degree of variability in a value or range, for example, within 10%, within 5%, or within 1% of a stated value or of a stated limit of a range.

In the methods of the present disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

EXAMPLES

Analytical Methods

Conventional bulk parameters were obtained according to ASTM methods as follows: (1) standard test methods for simulated distillation, density, and total sulfur according to ASTM methods D7169, D4052, and D4294, respectively; (2) separation of the entire sample into aromatic ring number fractionations using high performance liquid chromatography (HPLC) with refractive index detection (RID), and (3) chemical bulk characterization using nuclear magnetic resonance (NMR) spectroscopy.

HPLC: Normal-phase liquid chromatographic separation was based on the principle of ASTM D6591 (IP 548). An Agilent 1200 HPLC system with a binary pump, a degasser, an auto sampler was used for the separation over amino-propano-bonded silica stationary phase and detection was achieved with ultraviolet light selective and refractive index detection (UVDAD and RID). Instrument control and data recording were performed using Chemstation software, Agilent Technologies. An HPLC column (250×4.6 mm) packed with LiChrospher 100-5 NH2 was obtained from KNAUER, Germany. The average particle size and pore diameter for the silica packing material were 5 μm and 100 Å, respectively. The following HPLC conditions were maintained: mobile phase: n-heptane, column oven temperature: 35° C., flow rate: 0.8 mL/min, and run time: 60 minutes. All the samples were diluted (1:10) with n-heptane and filtered through a 0.22 μm syringe filter prior to analysis. The relative abundance of different hydrocarbon species was estimated by normalization of each peak area to the sum of all peak areas (saturates and aromatics). The refractive index of each detected species was higher than the refractive index of n-heptane (1.387). Therefore, this method did not consider species which had a refractive index lower than that of n-heptane. Group identification was based on the retention times of standard compounds and detection by refractive index for saturates, and the UV light absorption at various wavelengths for the aromatic ring number groups, i.e., 254 nm for monoaromatics, 300 nm for diaromatics, and 340 nm for tri+ aromatics.

NMR: Samples were measured after dilution in deuterated chloroform ($CDCl_3$). Quantitative $^1H$ and $^{13}C$ NMR spectra were acquired on a JEOL 500 MHZ NMR spectrometer, equipped with a 5 mm liquids probe.

GC×GC: Determination of hydrocarbons was conducted using 2-dimensional gas chromatography (GC×GC). Two-dimensional gas chromatograms were obtained using 7890 Agilent GCs (Agilent Technologies, Santa Clara, California, USA), both modified with single loop modulation systems from Zoex (ZX1 model, Zoex Corporation, Houston, Texas, USA). The GC was equipped with an FID from Agilent (Santa Clara, California, USA) operated as recommended by the manufacturer. 0.5 μL samples were injected using a split/splitless injector operated at 300° C., and a split ratio of 100:1. The separation was performed at a constant flow of 1.0 ml/min, using a first polydimethylsiloxane column (50 m length, 0.250 mm internal diameter, 250 μm film thickness) and a second polyethylene glycol column (1.7 m length, 0.1 mm internal diameter, 100 μm film thickness). The initial oven temperature of 40° C. was ramped to 280° C., at a rate of 2° C./min, before being kept isothermal for 15 mins. Data processing was achieved using software (Zoex Corporation, Houston, Texas). The chromatographic identification of compounds was based on retention times. Quantification was achieved by normalization of the chromatogram to the total chromatogram area.

GC-FIMS: Gas chromatography-field ionization high resolution mass spectrometry (GC-FIMS) was conducted on a Jeol accutof consisting of an Agilent 7890 gas chromatograph hyphenated via field ionization probe (FI) to a time of flight mass spectrometer. The GC was operated in standard configuration without modulation or second column. The GC was set up with at SGE BPX50 column, 60 length, 0.25 mm inner diameter, and 0.25 μm film thickness. 1 μL of the sample was injected at 50:1 split ration, diluted 1 to 3 v/v in toluene. The injector was kept at 280° C., and a flow of 0.7 mL/min of helium gas was maintained. The oven temperature program was as follows: 60 m column: 30° C. for 2 min, ramped by 10° C./min to 150° C., then ramped by 5° C./min to 330° C., which was held for 10 min. The interface to the mass spectrometer was kept at 310° C., corresponding to the maximum temperature attainable, and the ion chamber was heated to 150° C. Ionization was achieved using a field emitter (Jeol) at 40 mA current. Ions were recorded between 35-700 m/z, at 2.5 Hz scan rate. Before analysis the ion extraction and transfer parameters were tuned using acetone as standard bled into the ion chamber through the built-in needle valve. Data processing consisted of peak centroid picking at 100 counts threshold (arbitrary units) with a 70% centroid calculation threshold. Recalibration of the m/z scale was done on the alkane series (DBE=0) before exporting the data as netCDF type. The netCDF data were noise filtered using a custom-built algorithm (python 3.10.3, with pandas, numpy, netCDF4 packages), then compounds were identified using precalculated Kendrick mass tables for compound identification. Chromatographic retention times were employed to differentiate between sulfur and hydrocarbon families.

FT-ICR MS: High resolution mass spectra were acquired using a 12 T Solarix FT-ICR mass spectrometer (Bruker Daltonics, Bremen, Germany) equipped with an Apollo II ion source, operated in positive APPI mode. Specific parameters for this work were as follows: Ions were accumulated in the collision cell (h2) for 0.1 s before transfer to the ICR cell for high resolution mass measurement, with funnel RF voltage tuned between 80 V and 190 V, typically 110 V, and a typical ion transfer time of 0.800 ms. 100 scans with 8M data points were recorded and processed to identify peaks above 3 times the signal-to-noise ratio. Only radical cations [M•+] and their $^{13}C$ and $^{34}S$ isotope signals were considered. Aromatic compounds are speciated using APPI FT-ICR MS. The HPNA were identified by summing the corresponding species (corresponding to a specific carbon number vs. double bond equivalent range) as a fraction of all APPI identified species.

Example 1. Hydrocarbon Sample Analysis

A sample of partially hydrotreated Arabian Medium crude was analyzed. The results shown below are representative for other treated crude oil samples.

First Portion Composition: Detailed Hydrocarbon Analysis (DHA)

The DHA results were compounded into paraffins, and naphthenic and aromatic rings. For each group, the weight averaged carbon number was calculated. Saturated rings were assumed to be 1 and aromatic rings were also set to 1.

Results are shown in Table 1, where each row describes one representative species (PARA, NAPH, and ARO). The number of carbon atoms is in the first data column to the left (C), followed from left to right by alkyl-chain carbon atoms (PARA), saturated rings (NR), aromatic rings (AR), and sulfur atoms(S).

TABLE 1

Representative Species of First Portion

| | C | PARA | NR | AR | S |
|---|---|---|---|---|---|
| PARA | 8.0† | 8‡ | | | |
| NAPH | 8.0† | 2‡ | 1† | | |
| ARO | 7.0† | 1‡ | 0† | 1† | |

†Determined by DHA;
‡Calculated based on speciation data

Second Portion Composition: 2-Dimensional Gas Chromatography (GC×GC)

The GC×GC results were grouped by carbon number, number of saturated rings, and number of aromatic rings into 7 representative species as follows: Compounds with 1 and 2 aromatic rings were counted as aromatics (ARO), and 3+ aromatic-ringed compounds were accounted for separately as polyaromatics (3+ARO). The weight average number of saturated rings was calculated for naphthenes, and separately for aromatics and polyaromatics. The weight averaged number of aromatic rings was also calculated for aromatics and polyaromatics separately. If sulfur-containing compounds were identified, those were treated separately as sulfur-containing aromatics (ARO_S) and sulfur-containing polyaromatics (3+ARO_S). 4+ aromatic-ringed compounds with up to 3 alkyl-chain carbon atoms were accounted for separately as HPNA. For each of the 7 representative species, the weight averaged carbon number (C), saturated rings (NR) and aromatic rings (AR) were calculated. Results are shown in Table 2.

TABLE 2

| Representative Species of Second Portion | | | | | |
|---|---|---|---|---|---|
| | C | PARA | NR | AR | S |
| PARA | 15.0† | 15‡ | | | |
| NAPH | 15.0† | 9‡ | 1† | | |
| ARO | 17.0† | 7‡ | 1† | 1† | |
| ARO_S | 15.0† | 7‡ | 1† | 1† | 1† |
| 3+ARO | 15.0† | 1‡ | 0 | 3† | |
| 3+ARO_S | 13.0† | 1‡ | 0 | 3† | 1† |
| HPNA | 15.0† | 1‡ | | 3† | |

†Determined by GCxGC;
‡Calculated based on speciation data

Third Portion Composition: Gas Chromatography Field Ionization Mass Spectrometry (GC-FIMS)

The GC-FIMS results were grouped by carbon number, number of saturated rings, and number of aromatic rings into 7 representative molecular species, similarly to the GC×GC results above. If disulfur-containing compounds were detected, the weight averaged number of sulfur atoms was calculated for sulfur-containing polyaromatics. Results are shown in Table 3.

TABLE 3

| Representative Species of Third Portion | | | | | |
|---|---|---|---|---|---|
| | C | PARA | NR | AR | S |
| PARA | 28.0† | 28‡ | | | |
| NAPH | 32.0† | 22‡ | 2† | | |
| ARO | 35.0† | 25‡ | 1† | 1† | |
| ARO_S | 26.0† | 14‡ | 1† | 2† | 1† |
| 3+ARO | 35.0† | 21‡ | 0† | 3† | |
| 3+ARO_S | 26.0† | 14‡ | 0† | 3† | 1† |
| HPNA | 24.0† | 2‡ | | 5† | |

†Determined by GC-FIMS;
‡Calculated based on speciation data

Fourth Portion Composition: Fourier Transform Ion Cyclotron Resonance Mass Spectrometry (FT-ICR MS)

Similarly to the GC×GC and GC-FIMS results above, the APPI FT-ICR MS results were grouped by carbon number, number of saturated rings, and number of aromatic rings into 7 representative species. The alkyl-chain carbon number was extrapolated from the weight averaged total carbon number of hydrocarbon class species. For the representative polyaromatic sulfur species, the weight averaged number of sulfur atoms was calculated based on the sulfur and 3+ sulfur classes ($S_1$ to $S_5$). Results are shown in Table 4.

TABLE 4

| Representative Species of Fourth Portion | | | | | |
|---|---|---|---|---|---|
| | C | PARA | NR | AR | S |
| PARA | 44.0† | 44‡ | | | |
| NAPH | 44.0† | 30‡ | 3† | | |
| ARO | 41.0† | 27‡ | 1† | 2† | |
| ARO_S | 42.0† | 30‡ | 1† | 2† | 1† |
| 3+ARO | 48.0† | 26‡ | 1† | 4† | |
| 3+ARO_S | 42.0† | 22‡ | 1† | 4† | 1† |
| HPNA | 32.0† | 2‡ | | 7† | |

†Determined by FT-ICR MS;
‡Calculated based on speciation data

Mass Fraction of Portions: Fitting to Simulated Boiling Profile

The mass fraction of each compositional lump was tuned to match the recovery according to simulated distillation. The SIMDIS recovery against temperature was entered (in ° C.), see Table 5. Recovery was added against the final temperature, if less than 1.

TABLE 5

| Fit to Simulated Distillation | |
|---|---|
| D2887/D7169 (° C.) | recovery |
| 67.7 | 0.00 |
| 127.2 | 0.05 |
| 153.5 | 0.10 |
| 201.3 | 0.20 |
| 238.9 | 0.30 |
| 279.0 | 0.40 |
| 316.3 | 0.50 |
| 362.1 | 0.60 |
| 410.8 | 0.70 |
| 469.6 | 0.80 |
| 551.8 | 0.90 |
| 613.1 | 0.95 |
| 723.1 | 1.00 |

Each portion's boiling point (AEBP) was calculated based on the representative species data; an estimated recovery is shown in the bottom row, see Table 6.

TABLE 6

| Estimated Recovery | | |
|---|---|---|
| AEBP | C# | Recovery up to fraction |
| 150 | 8 | 0.08 |
| | estimated | 0.06 |

Figure 3:
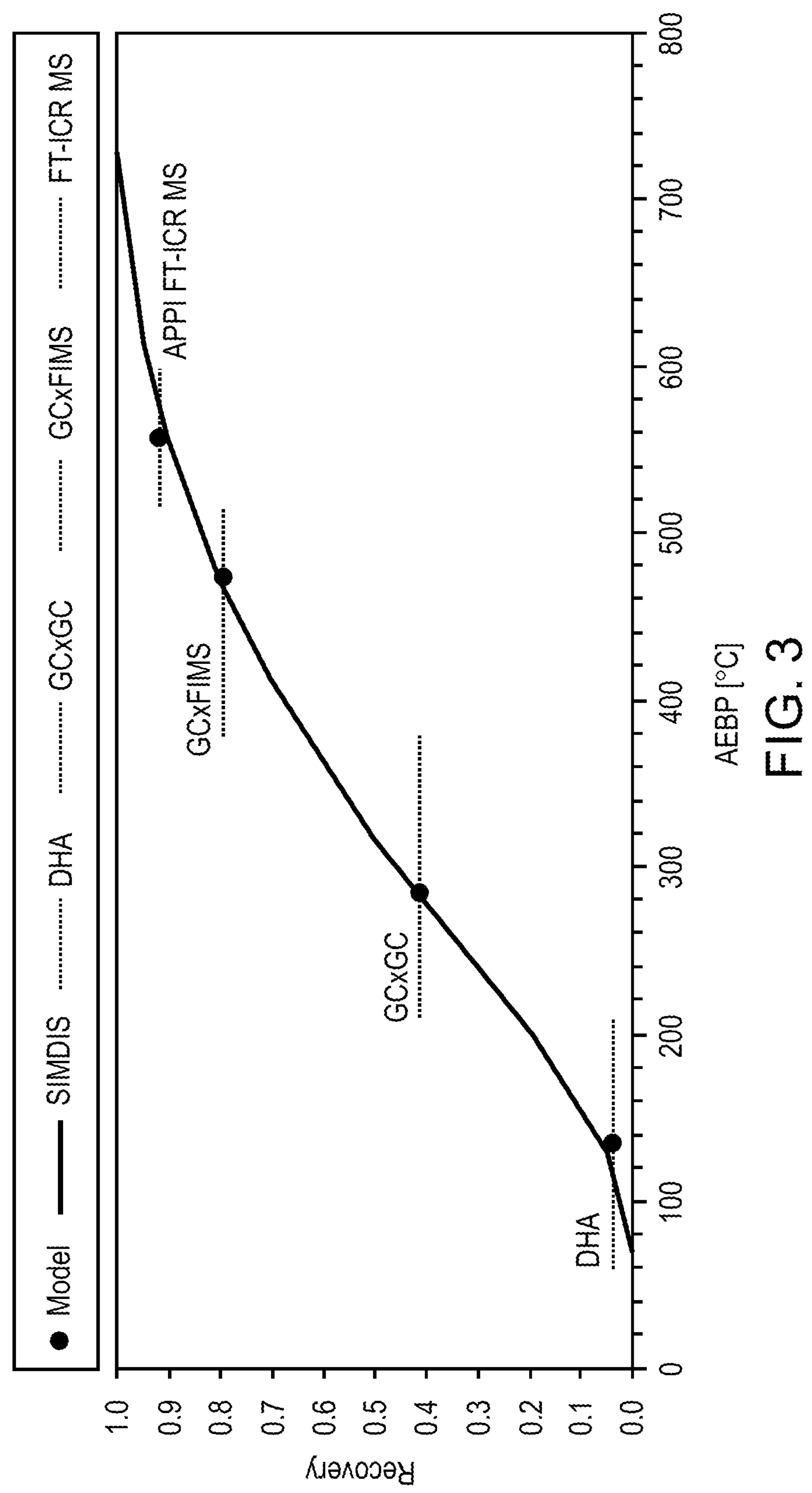
FIG. 3 is a plot showing the calculated boiling point of each portion of a hydrocarbon sample and the simulated boiling profile of the sample calculated according to an embodiment of the present disclosure

The fit of the portions to the boiling curve is shown in FIG. 3.

Mass Fraction of Representative Species: Fitting to Bulk Parameters

A number of bulk parameters were entered as targets for the optimization of individual representative species' mass fractions. The elemental composition was entered through the total sulfur (TS) and total hydrogen (TH) contents, whereby the total carbon (TC) content was derived as the balance. Atomic diversity was represented through (i) carbon groups obtained by $^{13}C$ NMR spectroscopy, namely paraffinic, naphthenic, and aromatic carbon mole fractions, and (ii) the mole fraction of aromatic hydrogen obtained by $^{1}H$ NMR spectroscopy. Aromatic rings were approximated from HPLC fractions for 1, 2, and 3+ aromatic ring compounds. Parameter weights and target values for the bulk parameters are shown in Table 7.

TABLE 7

| Bulk Parameters - Target Values and Weights | | | | | |
|---|---|---|---|---|---|
| | 13C NMR | | | 1H NMR | |
| | C(PARA) | C(NAP) | C(ARO) | H(SAT) | H(ARO) |
| target | 0.516† | 0.341† | 0.144† | 0.971‡ | 0.029† |
| weight | 1 | 1 | 100 | 1 | 1 |

TABLE 7-continued

| Bulk Parameters - Target Values and Weights | | | | | | |
|---|---|---|---|---|---|---|
| | | ARO-RING HPLC | | | | |
| | SATS | 1R 0.343† | 2R 0.093† | 3 + R 0† | TS S | TH H |
| target | 0.564‡ | 0.436‡ | | | 0† | 0.1367† |
| weight | 10 | 0 | 0 | 0 | 1 | 1 |

†Measured data;
‡Derived properties

Excel Solver's Generalized Reduced Gradient (GRG) algorithm with default settings was used to minimize the objective function. This solver method takes the slope of the objective function as the input values change and determines to have reached a solution when the partial derivatives equal zero. For the developed problem, the GRG algorithm led to highly reproducible results, however, the process was highly dependent on the initial mass fractions upon start and could become stuck at a local optimum depending on initial conditions. The initial conditions, therefore, are reset before each optimization (set their numerical value=1).

Figure 4:
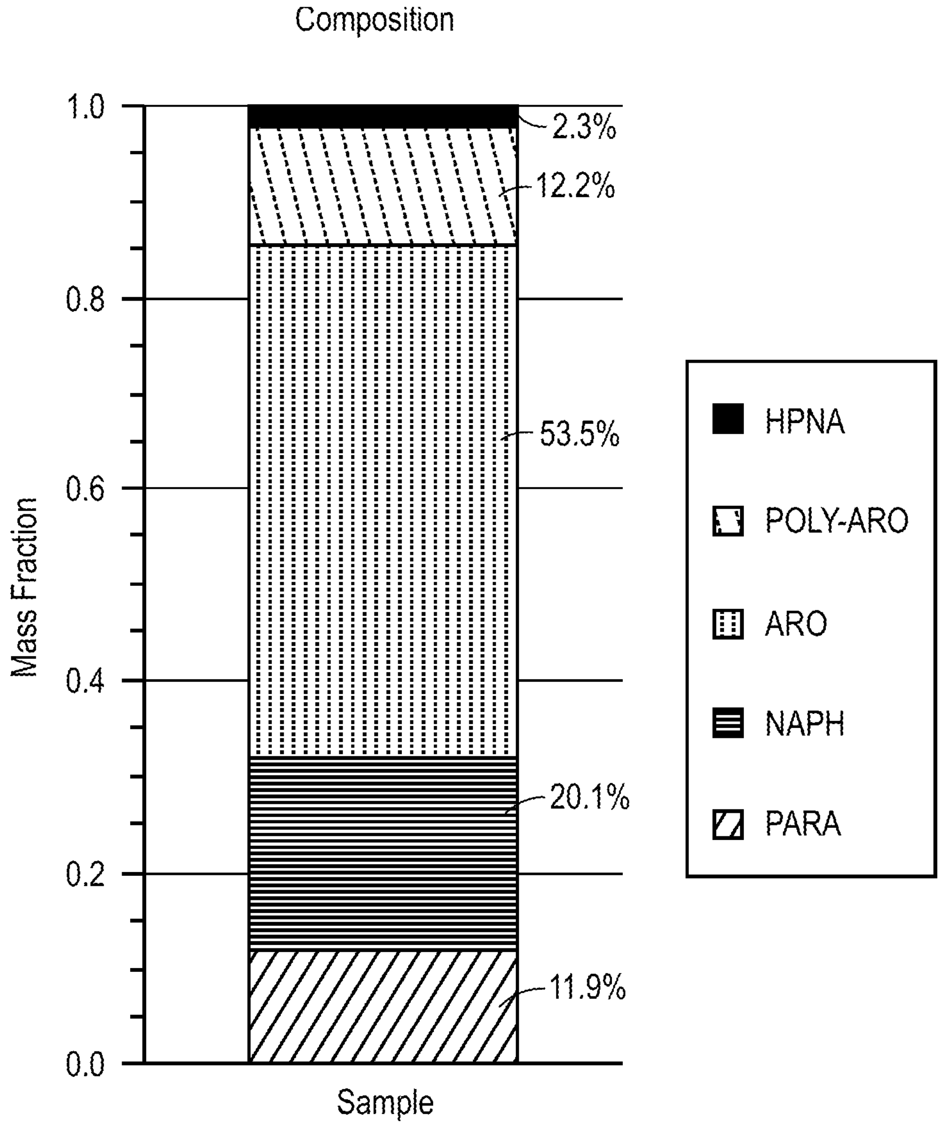
FIG. 4 is a graph showing the model output of a hydrocarbon analysis according to an embodiment of the present disclosure.
Figure 5:
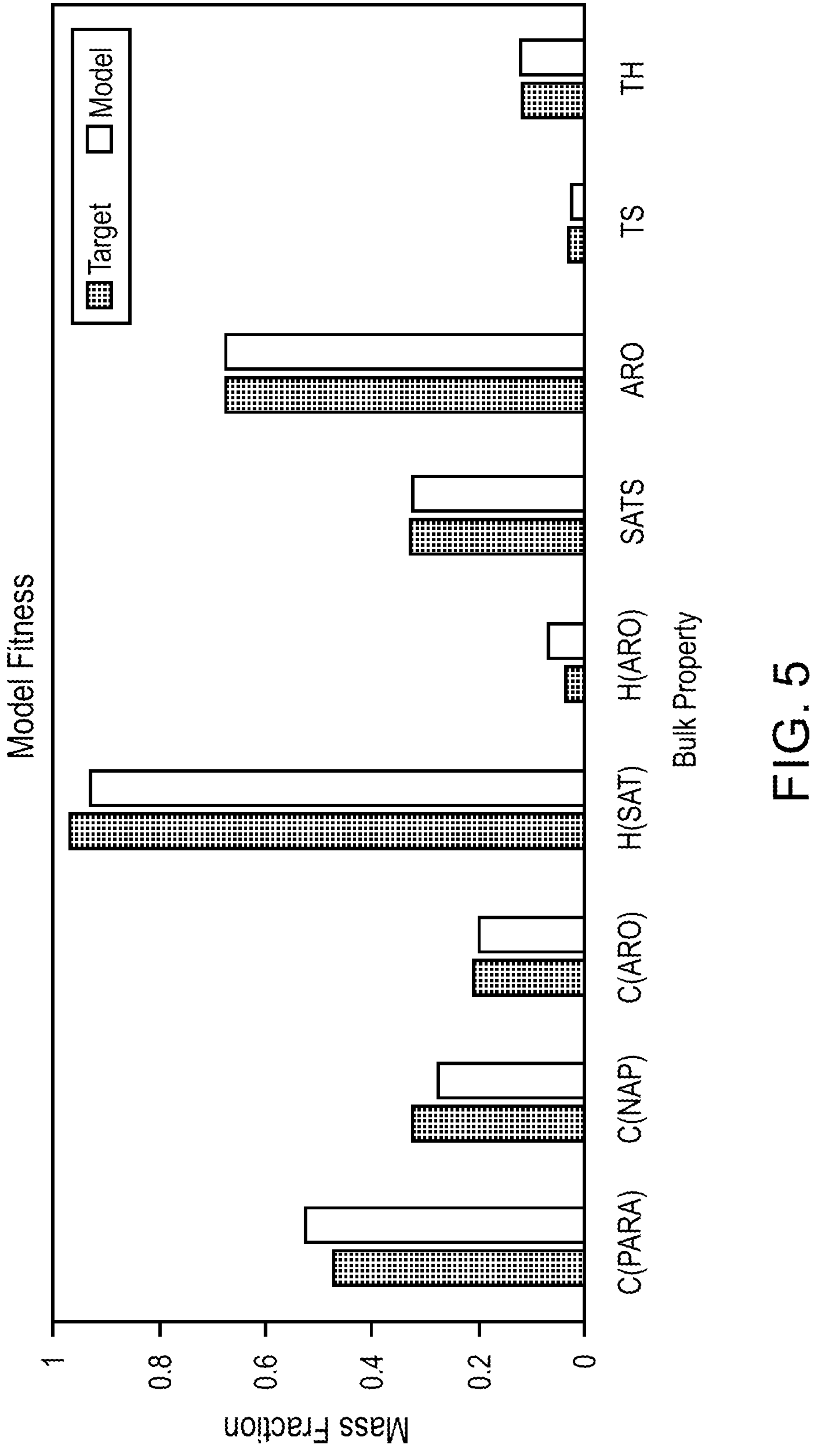
FIG. 5 is a graph showing the model fitness of an analysis according to an embodiment of the present disclosure.

The model was implemented in excel with the components described above. The average atom- and group-type properties that were calculated for each representative species were compounded into weight averaged values for each portion of the model. Optimization of the mole fractions was achieved automatically via solver algorithm, to minimize the total fitness score. This score was obtained as the weight averaged standard deviation of the calculated bulk parameters (weighted by each portion's relative mass fraction) against the target properties. The model output, including mass fractions of paraffins (PARA), naphthenes (NAPH), aromatics (ARO), polyaromatics (3+ARO), and heavy polynuclear aromatics (HPNA) is shown in FIG. 4, and the model fitness assessed against the target properties is shown in FIG. 5.

Validation

The model composition was assessed for crude oils grades (AXL to AH) and hydrotreated products thereof and found to represent bulk properties within the expected uncertainty.

Figure 6:
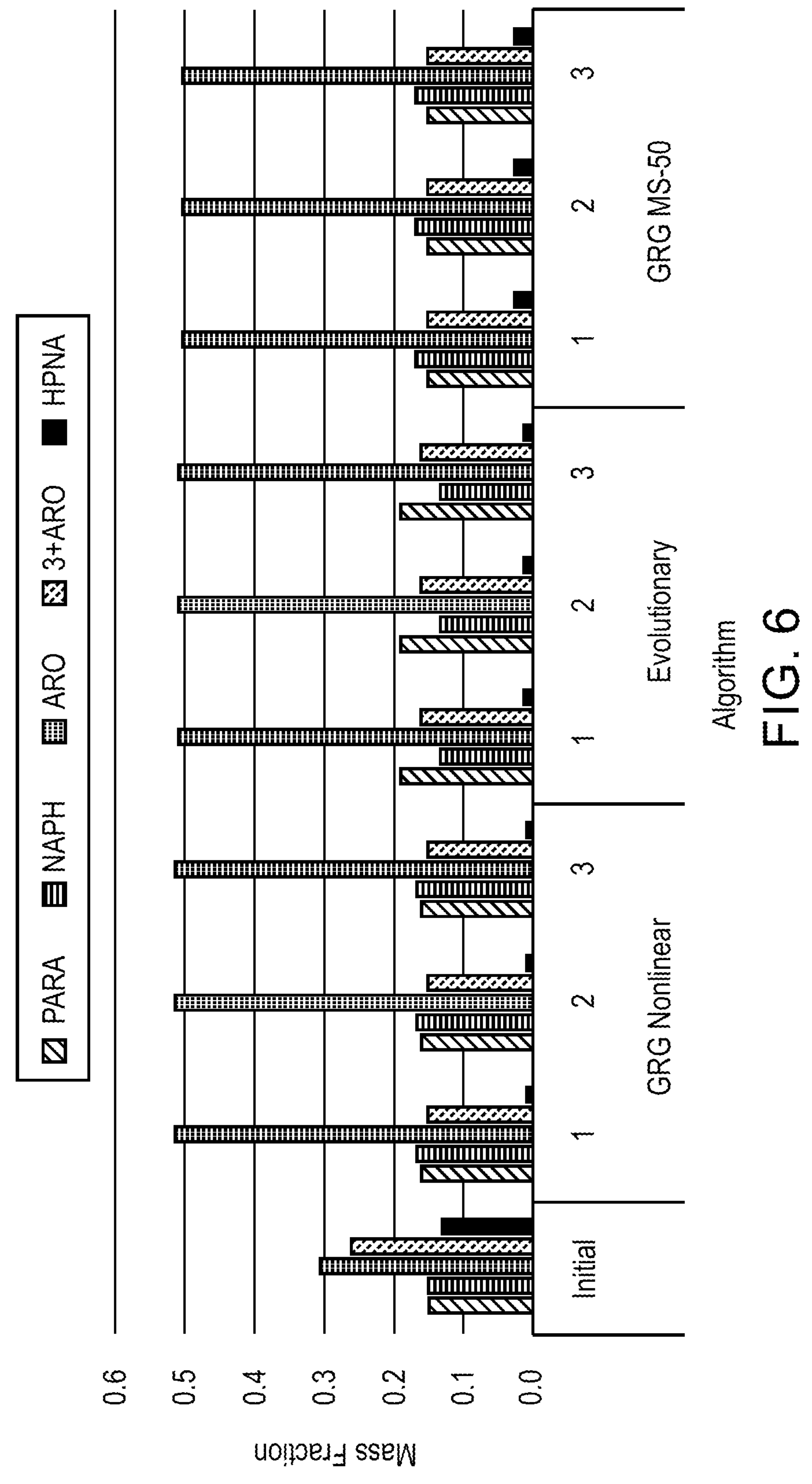
FIG. 6 is a graph showing the initial mass fractions for AM crude oil and analysis results after optimization using different algorithms according to an embodiment of the present disclosure.
Figure 7:
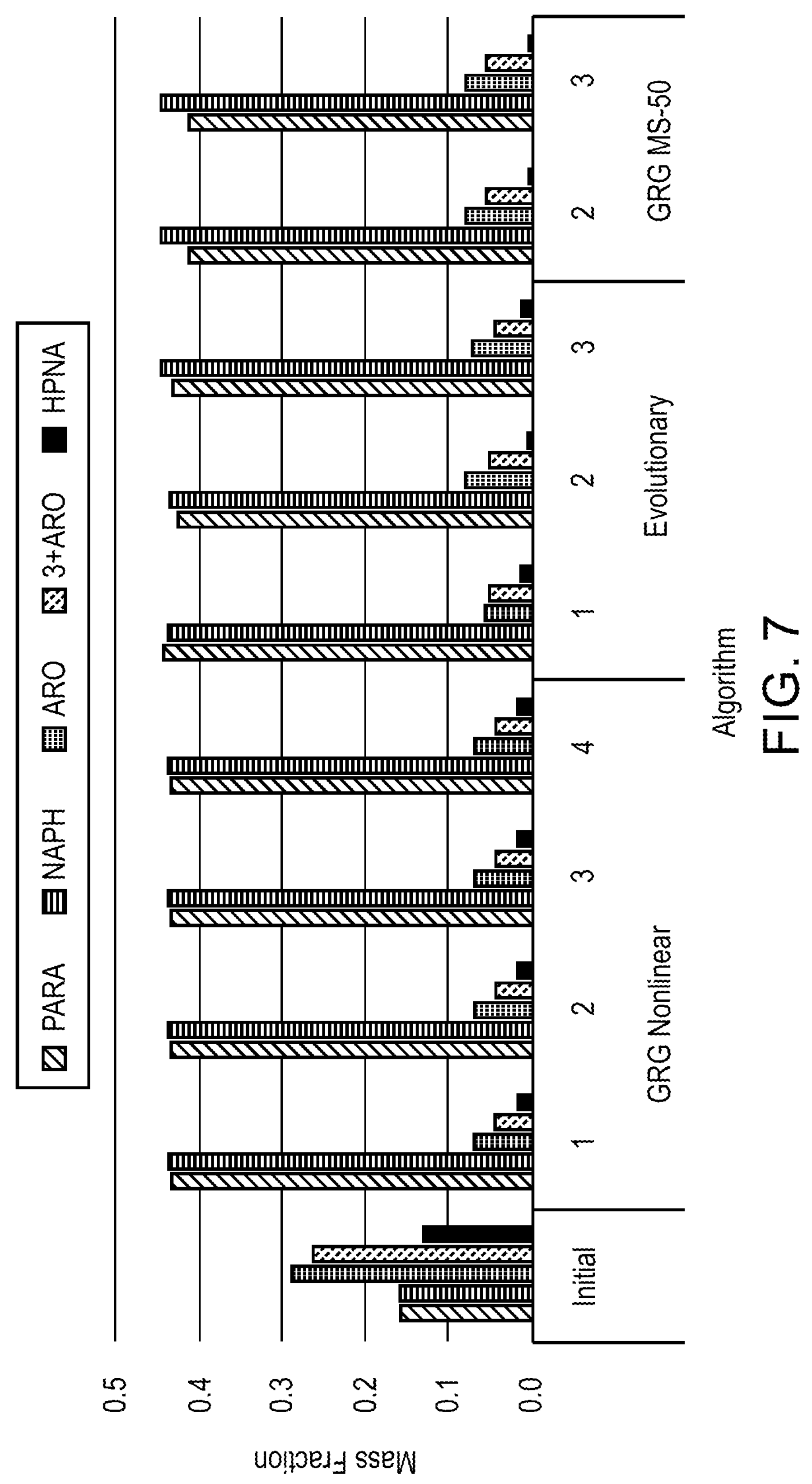
FIG. 7 is a graph showing the initial mass fractions for hydrotreated AM crude oil and analysis results after optimization using different algorithms according to an embodiment of the present disclosure.
Figure 8:
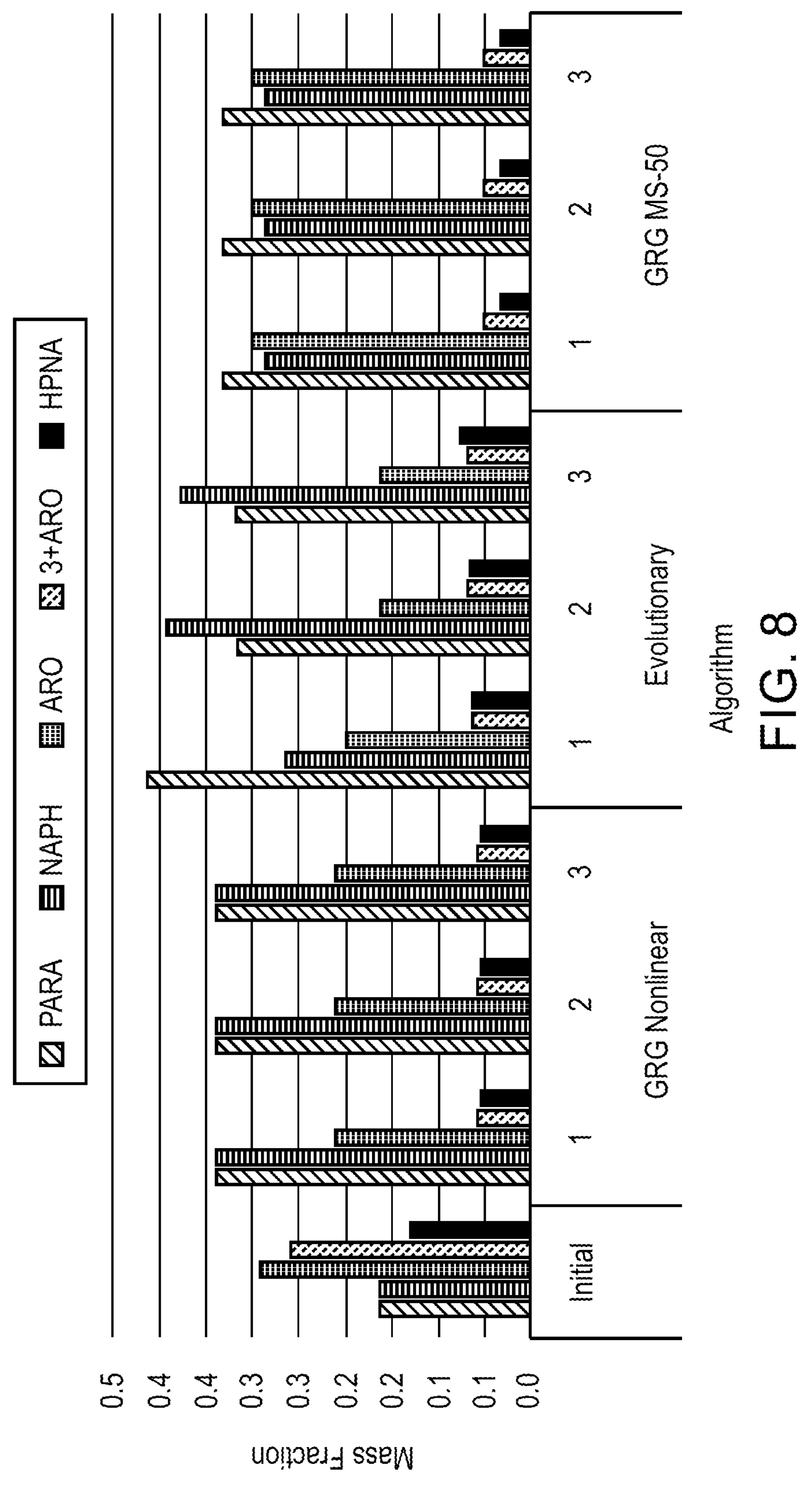
FIG. 8 is a graph showing the initial mass fractions for hydrotreated AM crude oil and analysis results after optimization using different algorithms according to an embodiment of the present disclosure.

The impact of different solver algorithms (GRG nonlinear, evolutionary, and GRG MS-50) was evaluated for AM crude oil and two samples of hydrotreated AM crude oil, as shown in FIGS. 6-8, respectively. Before starting each optimization, the initial mass fractions were equalized by setting all starting values to 1. The GRG nonlinear algorithm converged consistently with the fastest processing time. The Evolutionary algorithm showed inconsistent results with long processing times. It is possible that a wider set of starting parameters could have improved consistency, but this option was impractical due to the longer run times. The GRG nonlinear algorithm with 50 parallel starts (MS-50) showed consistent results.

Figure 9:
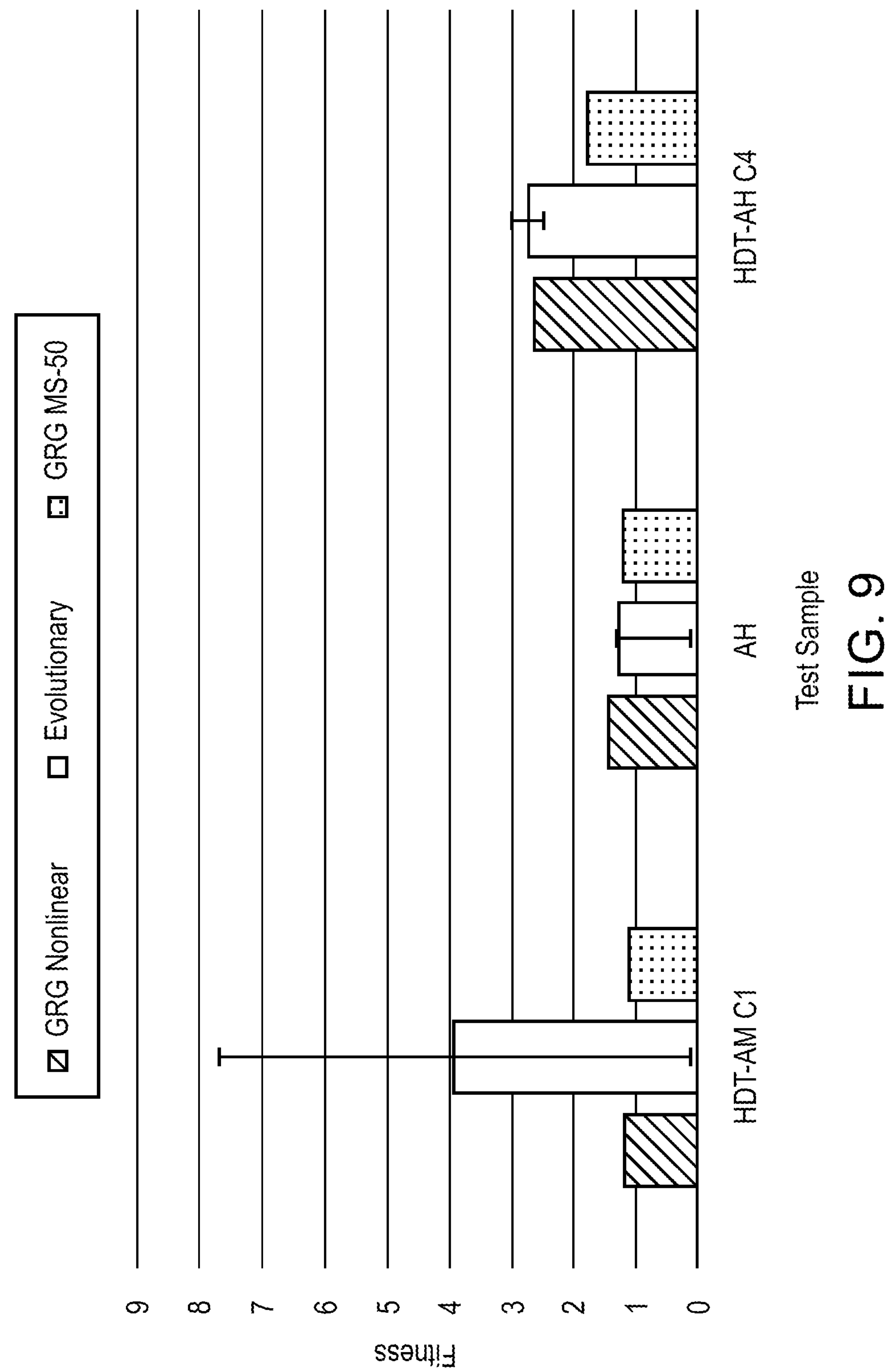
FIG. 9 is a graph showing the fitness and variation of results for hydrocarbon analyses according to an embodiment of the present disclosure.

The fitness was expressed as the standard deviation of the modelled composition against weighted target parameters. The fitness and variation of results for three test samples are shown in FIG. 9. The results show that GRG nonlinear and GRG nonlinear with 50 multistarts (MS-50) converge onto a stable solution.

Example 2. Application to Optimization of Hydrotreating Conditions

Hydrotreating (HDT) of AM crude oil under 5 different conditions (C1-C5) was assessed as a pretreatment for the FCC conversion of the oil into chemicals. For this purpose, the chemical composition of the liquid HDT products was determined according to Example 1. The comparison of the reactive groups allows a ranking of the HDT conditions by their products' expected FCC reactivity; the most reactive FCC feedstock compositions are attained under more severe HDT conditions such as high temperature, low LHSV, and correspondingly long residence times.

Figure 10:
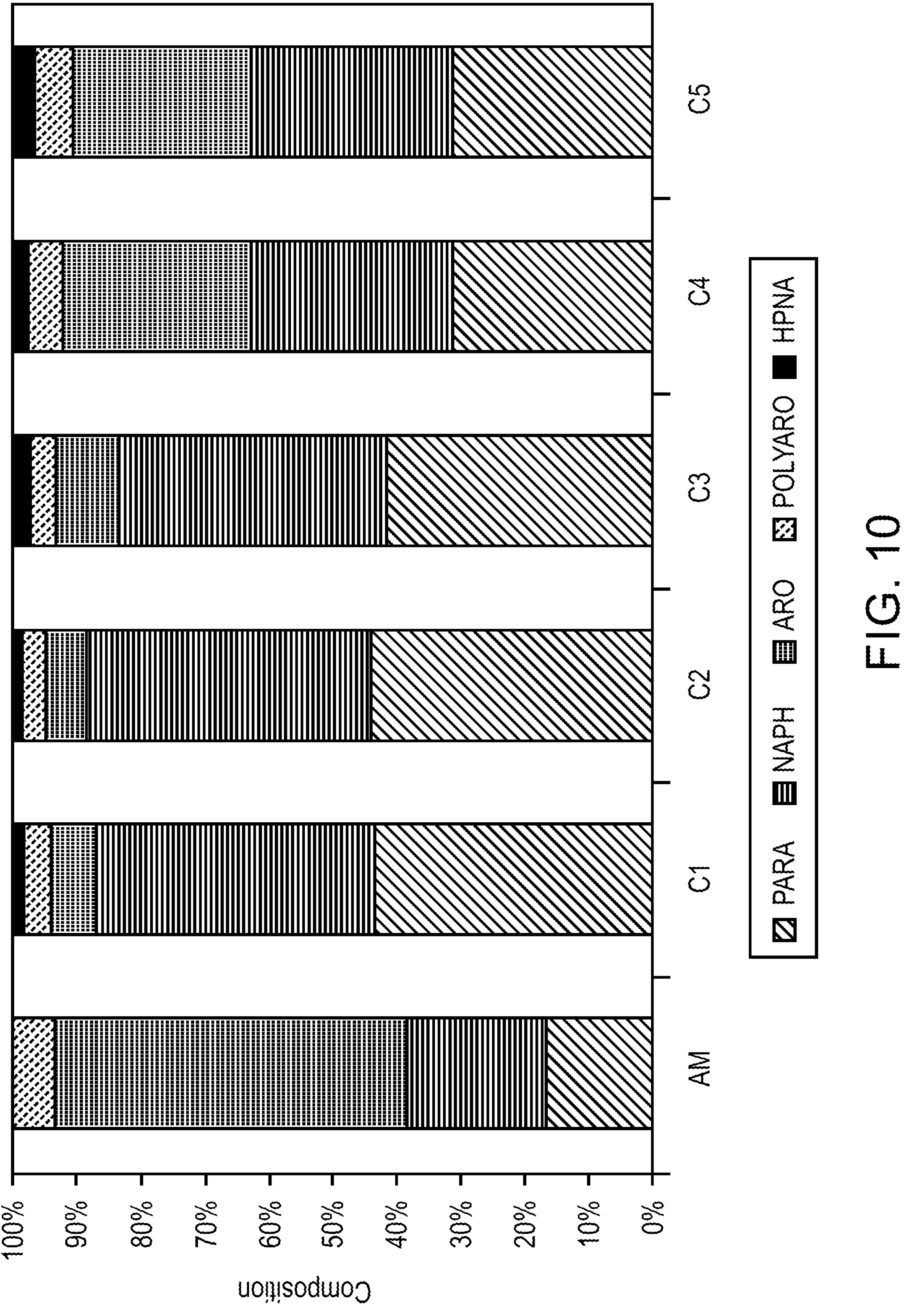
FIG. 10 is a graph showing the model output of hydrocarbon analyses according to an embodiment of the present disclosure.

Results, including mass fractions of paraffins (PARA), naphthenes (NAPH), aromatics (ARO), polyaromatics (POLYARO), and heavy polynuclear aromatics (HPNA) are shown in FIG. 10 and provided in numerical form in Table 8.

TABLE 8

| Model Output for Crude Oil and Treated Oil Samples | | | | | | |
|---|---|---|---|---|---|---|
| | AM | C1 | C2 | C3 | C4 | C5 |
| PARA | 0.167 | 0.435 | 0.442 | 0.417 | 0.310 | 0.313 |
| NAPH | 0.215 | 0.437 | 0.445 | 0.419 | 0.318 | 0.317 |
| ARO | 0.551 | 0.069 | 0.062 | 0.099 | 0.295 | 0.279 |
| POLYARO | 0.066 | 0.043 | 0.036 | 0.038 | 0.053 | 0.060 |
| HPNA | 0.000 | 0.017 | 0.015 | 0.027 | 0.024 | 0.031 |

Figure 11:
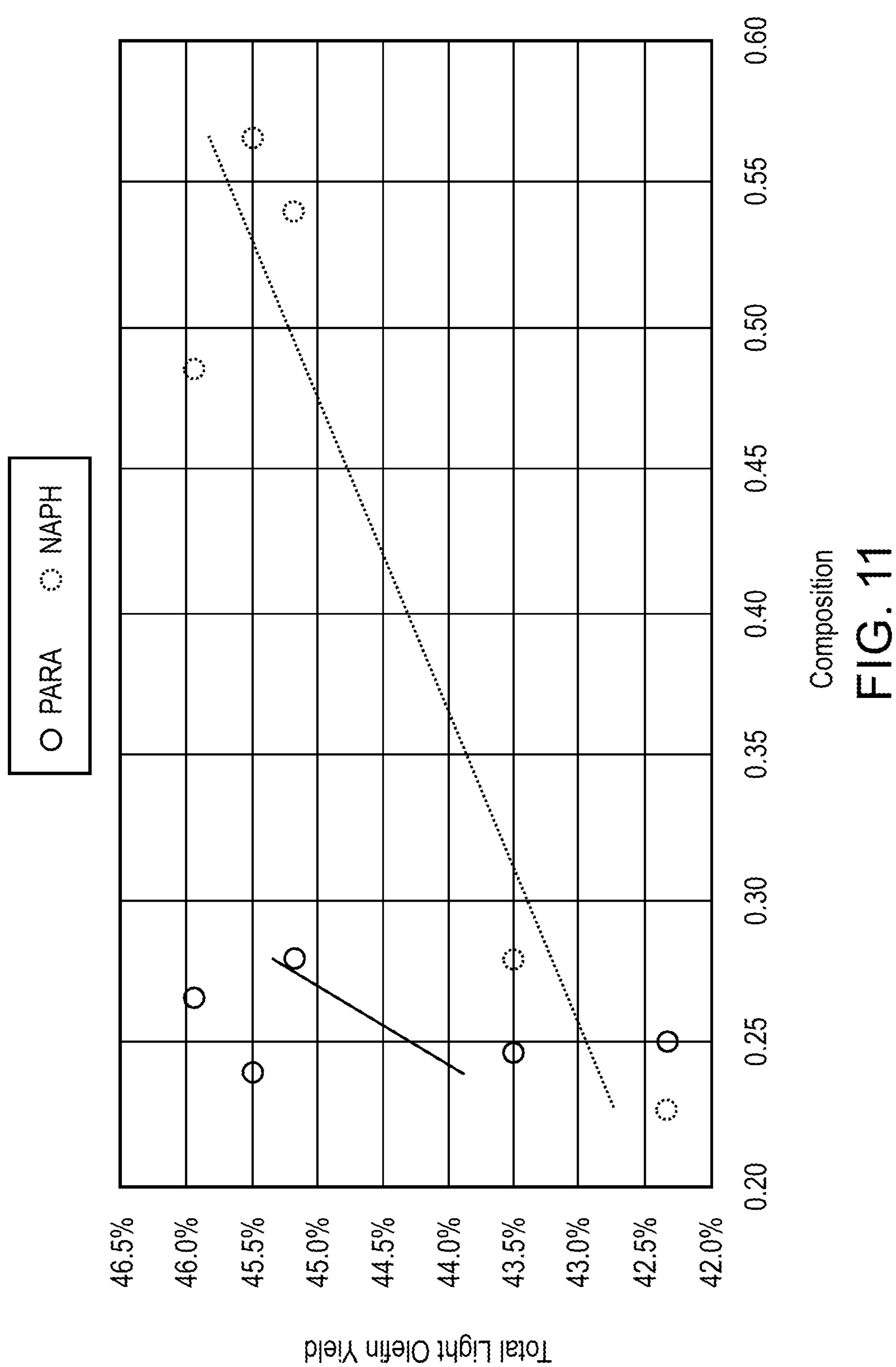
FIG. 11 is a plot showing the light olefin yield of hydrocarbon feedstocks after FCC processing.
Figure 12:
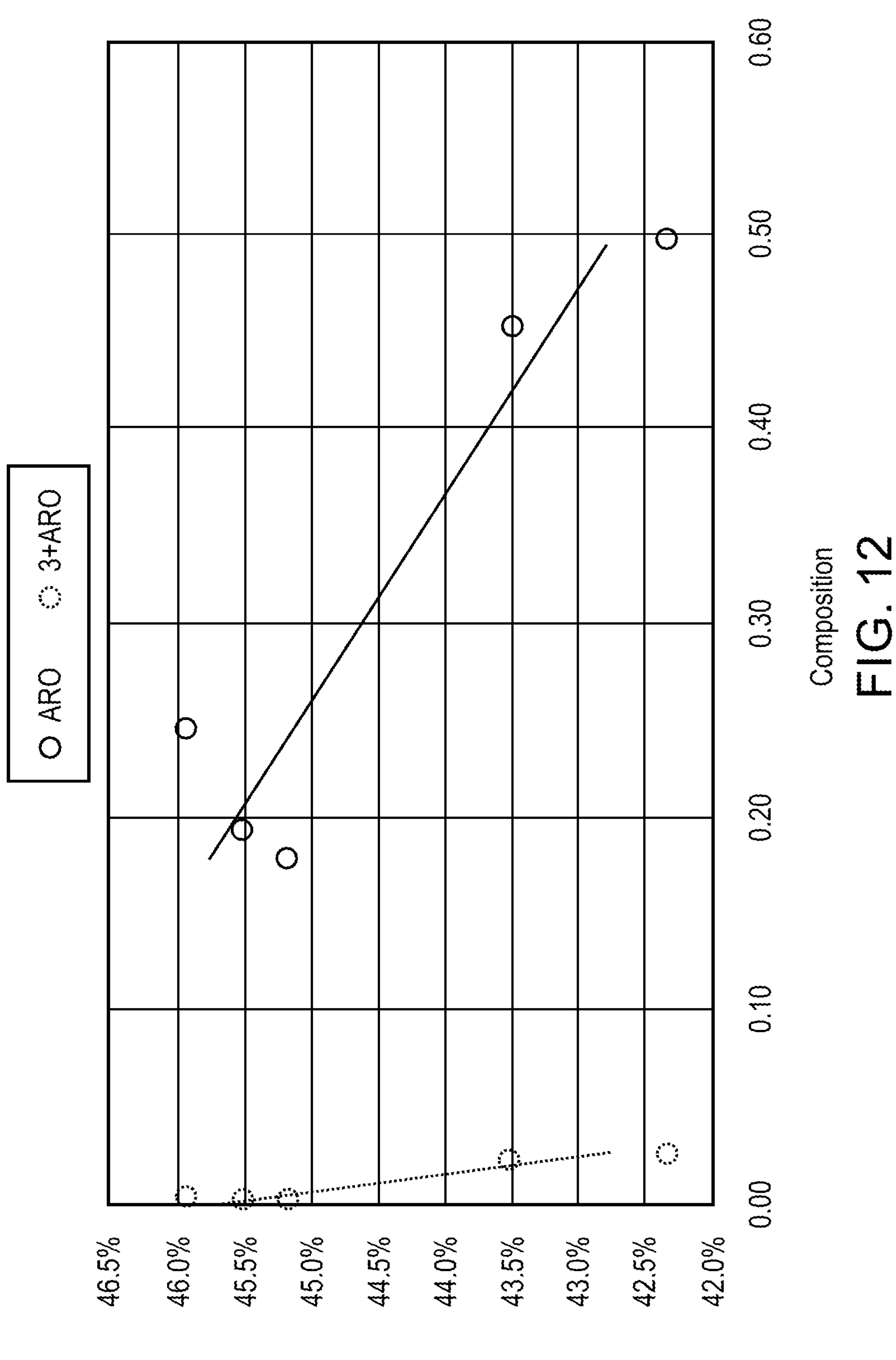
FIG. 12 is a plot showing the impact of aromatic and polyaromatic groups on feedstock reactivity.

Overall, the hydrotreating conditions impacted the samples' chemical compositions significantly; the samples were ordered in terms of prospective FCC reactivity from C3 (most promising feedstock)>C2>C1>C4>C5 (least promising feedstock). All hydrotreated samples had preferable chemical compositions when compared to the untreated crude oil (AM). FIG. 11 shows the light olefin yield of the hydrotreated feedstocks after FCC processing. The paraffin content variation in the feedstocks appeared too low to make a difference, but the naphthenes contents varied and positively correlated with light olefin yield. FIG. 12 shows the impact of aromatic and polyaromatic groups on reactivity; both groups negatively affected light olefin production.

Embodiments

Certain embodiments of the present disclosure are provided in the following list:

Embodiment 1. A method of analyzing a hydrocarbon sample, comprising
- determining a representative composition of each of two or more portions of the sample, wherein each representative composition independently comprises one or more representative species;
- determining a mass fraction of each of the two or more portions present in the sample; and
- determining a mass fraction of each representative species present in each of the two or more portions of the sample, wherein each representative species is defined by
- a number of carbon atoms;
- a number of alkyl-chain carbon atoms;
- a number of saturated rings;
- a number of aromatic rings; and
- a number of sulfur atoms.

Embodiment 2. The method of embodiment 1, comprising
- determining a representative composition of a first portion of the sample;
- determining a mass fraction of the first portion present in the sample; and
- determining a mass fraction of each representative species present in the first portion of the sample.

Embodiment 3. The method of embodiment 2, wherein the first portion of the sample comprises a light-ends fraction.

Embodiment 4. The method of embodiment 2 or embodiment 3, comprising determining the representative composition of the first portion of the sample by detailed hydrocarbon analysis.

Embodiment 5. The method of any one of embodiments 2-4, wherein the one or more representative species of the first portion comprise a representative paraffin, a representative naphthene, a representative aromatic, or any combination thereof.

Embodiment 6. The method of any one of embodiments 2-5, comprising determining a representative composition of a second portion of the sample;

determining a mass fraction of the second portion present in the sample; and determining a mass fraction of each representative species present in the second portion of the sample.

Embodiment 7. The method of embodiment 6, wherein the second portion of the sample comprises a middle-boiling fraction.

Embodiment 8. The method of embodiment 6 or embodiment 7, comprising determining the representative composition of the second portion of the sample by 2-dimensional gas chromatography.

Embodiment 9. The method of any one of embodiments 6-8, wherein the one or more representative species of the second portion comprise a representative paraffin, a representative naphthene, a representative aromatic, a representative sulfur-containing aromatic, a representative polyaromatic, a representative sulfur-containing polyaromatic, a representative heavy polynuclear aromatic (HPNA), or any combination thereof.

Embodiment 10. The method of any one of embodiments 6-9, comprising determining a representative composition of a third portion of the sample;

determining a mass fraction of the third portion present in the sample; and determining a mass fraction of each representative species present in the third portion of the sample.

Embodiment 11. The method of embodiment 10, wherein the third portion of the sample comprises a high-boiling fraction.

Embodiment 12. The method of embodiment 10 or embodiment 11, comprising determining the representative composition of the third portion of the sample by gas chromatography field ionization mass spectrometry.

Embodiment 13. The method of embodiment 10 or embodiment 11, comprising determining the representative composition of the third portion of the sample by high-temperature two-dimensional gas chromatography with high-resolution mass spectrometry.

Embodiment 14. The method of any one of embodiments 10-13, wherein the one or more representative species of the third portion comprise a representative paraffin, a representative naphthene, a representative aromatic, a representative sulfur-containing aromatic, a representative polyaromatic, a representative sulfur-containing polyaromatic, a representative HPNA, or any combination thereof.

Embodiment 15. The method of any one of embodiments 10-14, comprising determining a representative composition of a fourth portion of the sample;

determining a mass fraction of the fourth portion present in the sample; and determining a mass fraction of each representative species present in the fourth portion of the sample.

Embodiment 16. The method of embodiment 15, wherein the fourth portion of the sample comprises a non-boiling fraction.

Embodiment 17. The method of embodiment 15 or embodiment 16, comprising determining the representative composition of the fourth portion of the sample by Fourier transform ion cyclotron resonance mass spectrometry.

Embodiment 18. The method of embodiment 15 or embodiment 16, comprising determining the representative composition of the fourth portion of the sample by liquid chromatographic fractionation followed by field desorption/field ionization time of flight mass spectrometry.

Embodiment 19. The method of any one of embodiments 15-18, wherein the one or more representative species of the fourth portion comprise a representative paraffin, a representative naphthene, a representative aromatic, a representative sulfur-containing aromatic, a representative polyaromatic, a representative sulfur-containing polyaromatic, a representative HPNA, or any combination thereof.

Embodiment 20. The method of any one of embodiments 1-19, comprising determining the mass fraction of each of the two or more portions present in the sample by fitting to a simulated distillation profile of the sample.

Embodiment 21. The method of any one of embodiments 1-20, comprising determining the mass fraction of each representative species present in each of the two or more portions of the sample by fitting to a bulk parameter of the sample.

Embodiment 22. The method of embodiment 21, wherein the bulk parameter comprises a carbon type distribution of the sample and a hydrogen type distribution of the sample.

Embodiment 23. The method of embodiment 22, further comprising determining the carbon type distribution of the sample and the hydrogen type distribution of the sample by nuclear magnetic resonance spectroscopy.

Embodiment 24. The method of any one of embodiments 21-23, wherein the bulk parameter comprises a saturated compound content of the sample and an aromatic compound content of the sample.

Embodiment 25. The method of embodiment 24, further comprising determining the saturated compound content and the aromatic compound content of the sample by high-pressure liquid chromatography.

Embodiment 26. The method of any one of embodiments 21-25, wherein the bulk parameter comprises a total hydrogen content of the sample and a total sulfur content of the sample.

Embodiment 27. The method of any one of embodiments 1-26, wherein the hydrocarbon sample comprises a crude oil.

Embodiment 28. The method of any one of embodiments 1-26, wherein the hydrocarbon sample comprises a hydrotreated crude oil.

Other implementations are also within the scope of the following claims.

What is claimed is:

1. A method of analyzing a hydrocarbon sample, comprising determining a representative composition of each of two or more portions of the sample, wherein each representative composition independently comprises one or more representative species;

determining a mass fraction of each of the two or more portions present in the sample; and determining a mass fraction of each representative species present in each of the two or more portions of the sample, wherein each representative species is defined by a number of carbon atoms;

a number of alkyl-chain carbon atoms;

a number of saturated rings;

a number of aromatic rings; and a number of sulfur atoms.

2. The method of claim 1, comprising determining a representative composition of a first portion of the sample;

determining a mass fraction of the first portion present in the sample; and determining a mass fraction of each representative species present in the first portion of the sample.

3. The method of claim 2, wherein the first portion of the sample comprises a light-ends fraction.

4. The method of claim 3, comprising determining the representative composition of the first portion of the sample by detailed hydrocarbon analysis.

5. The method of claim 3, wherein the one or more representative species of the first portion comprise a representative paraffin, a representative naphthene, a representative aromatic, or any combination thereof.

6. The method of claim 2, comprising determining a representative composition of a second portion of the sample;

determining a mass fraction of the second portion present in the sample; and determining a mass fraction of each representative species present in the second portion of the sample.

7. The method of claim 6, wherein the second portion of the sample comprises a middle-boiling fraction.

8. The method of claim 7, comprising determining the representative composition of the second portion of the sample by 2-dimensional gas chromatography.

9. The method of claim 7, wherein the one or more representative species of the second portion comprise a representative paraffin, a representative naphthene, a representative aromatic, a representative sulfur-containing aromatic, a representative polyaromatic, a representative sulfur-containing polyaromatic, a representative heavy polynuclear aromatic (HPNA), or any combination thereof.

10. The method of claim 6, comprising determining a representative composition of a third portion of the sample;

determining a mass fraction of the third portion present in the sample; and determining a mass fraction of each representative species present in the third portion of the sample.

11. The method of claim 10, wherein the third portion of the sample comprises a high-boiling fraction.

12. The method of claim 11, comprising determining the representative composition of the third portion of the sample by gas chromatography field ionization mass spectrometry.

13. The method of claim 11, comprising determining the representative composition of the third portion of the sample by high-temperature two-dimensional gas chromatography with high-resolution mass spectrometry.

14. The method of claim 11, wherein the one or more representative species of the third portion comprise a representative paraffin, a representative naphthene, a representative aromatic, a representative sulfur-containing aromatic, a representative polyaromatic, a representative sulfur-containing polyaromatic, a representative HPNA, or any combination thereof.

15. The method of claim 10, comprising determining a representative composition of a fourth portion of the sample;

determining a mass fraction of the fourth portion present in the sample; and determining a mass fraction of each representative species present in the fourth portion of the sample.

16. The method of claim 15, wherein the fourth portion of the sample comprises a non-boiling fraction.

17. The method of claim 16, comprising determining the representative composition of the fourth portion of the sample by Fourier transform ion cyclotron resonance mass spectrometry.

18. The method of claim 16, comprising determining the representative composition of the fourth portion of the sample by liquid chromatographic fractionation followed by field desorption/field ionization time of flight mass spectrometry.

19. The method of claim 16, wherein the one or more representative species of the fourth portion comprise a representative paraffin, a representative naphthene, a representative aromatic, a representative sulfur-containing aromatic, a representative polyaromatic, a representative sulfur-containing polyaromatic, a representative HPNA, or any combination thereof.

20. The method of claim 1, comprising determining the mass fraction of each of the two or more portions present in the sample by fitting to a simulated distillation profile of the sample.

21. The method of claim 1, comprising determining the mass fraction of each representative species present in each of the two or more portions of the sample by fitting to a bulk parameter of the sample.

22. The method of claim 21, wherein the bulk parameter comprises a carbon type distribution of the sample and a hydrogen type distribution of the sample.

23. The method of claim 22, further comprising determining the carbon type distribution of the sample and the hydrogen type distribution of the sample by nuclear magnetic resonance spectroscopy.

24. The method of claim 21, wherein the bulk parameter comprises a saturated compound content of the sample and an aromatic compound content of the sample.

25. The method of claim 24, further comprising determining the saturated compound content and the aromatic compound content of the sample by high-pressure liquid chromatography.

26. The method of claim 21, wherein the bulk parameter comprises a total hydrogen content of the sample and a total sulfur content of the sample.

27. The method of claim 1, wherein the hydrocarbon sample comprises a crude oil.

28. The method of claim 1, wherein the hydrocarbon sample comprises a hydrotreated crude oil.

* * * * *